(12) United States Patent
Burdulis et al.

(10) Patent No.: US 6,749,615 B2
(45) Date of Patent: Jun. 15, 2004

(54) APPARATUS AND METHODS FOR PERFORMING AN ANASTOMOSIS

(75) Inventors: Albert G. Burdulis, San Francisco, CA (US); Joshua M. Stafford, Fremont, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/171,139

(22) Filed: Jun. 13, 2002

(65) Prior Publication Data

US 2002/0198543 A1 Dec. 26, 2002

Related U.S. Application Data

(60) Provisional application No. 60/301,105, filed on Jun. 25, 2001.

(51) Int. Cl.⁷ .......................... A61B 17/04; A61B 17/10
(52) U.S. Cl. ........................................ 606/144; 139/148
(58) Field of Search .................... 81/335, 329, 338, 81/315, 420.5, 426, 426.5; 72/409.13, 409.14, 412, 416; 606/205, 139, 74, 113, 244, 248, 222, 224, 226, 227, 228

(56) References Cited

U.S. PATENT DOCUMENTS

| | | |
|---|---|---|
| 2,127,903 A | 8/1938 | Bowen |
| 4,164,225 A | 8/1979 | Johnson et al. |
| 4,182,339 A | 1/1980 | Hardy, Jr. |
| 4,553,543 A | 11/1985 | Amarasinghe |
| 4,651,733 A | 3/1987 | Mobin-Uddin |
| 4,803,984 A | 2/1989 | Narayanan et al. |
| 4,898,155 A | 2/1990 | Ovil et al. |
| 5,053,043 A | 10/1991 | Gottesman et al. |
| 5,104,399 A | 4/1992 | Lazarus |
| 5,364,408 A | 11/1994 | Gordon |
| 5,431,666 A | 7/1995 | Sauer et al. |
| 5,496,332 A | 3/1996 | Sierra et al. |
| 5,545,171 A | 8/1996 | Sharkey et al. |
| 5,554,162 A | 9/1996 | DeLange |
| 5,562,686 A | 10/1996 | Sauer et al. |
| 5,573,540 A | 11/1996 | Yoon |
| 5,779,719 A | 7/1998 | Klein et al. |
| 5,797,934 A | 8/1998 | Rygaard |
| 5,824,010 A | 10/1998 | McDonald |
| 5,860,990 A | 1/1999 | Nobles et al. |
| 5,868,763 A | 2/1999 | Spence et al. |
| 5,994,730 A | 11/1999 | Shrivastava et al. |
| 6,036,699 A | 3/2000 | Andreas et al. |
| 6,117,144 A | 9/2000 | Nobles et al. |
| 6,136,010 A | 10/2000 | Modesitt et al. |
| 6,190,396 B1 | 2/2001 | Whitin et al. |
| 6,280,460 B1 | 8/2001 | Bolduc et al. |
| 6,358,258 B1 | 3/2002 | Arcia et al. |
| 2003/0028202 A1 * | 2/2003 | Sancoff et al. ............... 606/144 |

FOREIGN PATENT DOCUMENTS

| | | |
|---|---|---|
| JP | 2-119866 | 10/1998 |
| SU | 1544383 | 9/1990 |
| WO | WO 00/59390 | 10/2000 |
| WO | WO 00/72764 A1 | 12/2000 |
| WO | WO 01/19259 | 3/2001 |
| WO | WO 02/36019 | 5/2001 |
| WO | WO 02/36021 | 5/2002 |

* cited by examiner

*Primary Examiner*—Julian W. Woo
*Assistant Examiner*—Paul A Roberts
(74) *Attorney, Agent, or Firm*—Joseph A. Twarowski

(57) ABSTRACT

A suturing device suitable for anastomosis procedures. The suturing device includes a suture guid and a needle holder. The suture guide includes a foot portion having an axis defined along a length of the foot portion. The foot portion includes a plurality of apertures, each aperture holding a suture. The needle holder movably holds at least one needle relative to a first side of the foot portion and movably holds at least one needle relative to a second side of the foot portion. The needles are movable into respective apertures, and the at least one needle on the first side of the foot portion is at an angle relative to the at least one needle on the second side of the foot portion.

9 Claims, 27 Drawing Sheets

APPARATUS AND METHODS FOR PERFORMING AN ANASTOMOSIS

This application claims the benefit of priority to Provisional Application No. 60/301,105, filed Jun. 25, 2001.

BACKGROUND OF THE INVENTION

The invention can be used advantageously to suture vessels, ducts, and the like, in a patient body. The invention can be used particularly advantageously in suturing blood vessels together during cardiac surgery, for example. Accordingly, the invention can be used during coronary artery bypass graft surgery (CABG), and the like. However, it is to be appreciated that the field of the invention is not to be limited to such uses only, but extends to suturing patient tissue together in general. For example, the invention can be used also to form sutures in bowel connections, femoral-popliteal artery anastomoses, and the like. It can also be used in the field of trauma closure, and the like.

It is often required to connect a vessel, duct, or the like, such as a hollow organ, or blood vessel, or the like, to a target piece of tissue, such as another vessel, duct, or the like. This is especially true in the case of certain types of cardiac surgery, such as CABG surgery. Often during such CABG surgery it is required to connect, or join, one blood vessel to another so that the vessels are joined together to be in fluid flow communication with each other. A joint formed between blood vessels in this fashion is often referred to as an anastomosis.

As is well known, the heart pumps blood through the body. The heart comprises a plurality of muscles which cooperate with one another to cause contractions of the heart thereby to provide a pumping action. The heart requires blood flow to its muscles to provide its muscles with the necessary oxygen, nutrients, and the like, necessary for muscular contraction. It often happens that one or more of the blood vessels which feed the heart muscles becomes diseased and develops a blockage, or becomes occluded, or the like. When this happens, a region of the heart normally fed by that diseased blood vessel can experience a depletion, or interruption, of blood supply. If such a condition is not treated in a timely fashion, the patient may suffer a heart attack with often fatal results.

CABG procedures are often performed to circumvent such a blockage, or occlusion, in a diseased blood vessel, thereby to provide the region of the heart normally fed by the diseased vessel with blood. This procedure normally involves tapping blood from an appropriate blood source, such as a donor blood vessel such as, for example, the aorta, saphenous vein, mammary artery, or the like, and routing the tapped blood to the diseased vessel downstream of the occlusion or blockage. A variety of procedures are currently employed to provide tapped blood downstream of an occlusion, or blockage, in a diseased blood vessel. One procedure involves making use of a graft. In such a case, an end of the graft is typically sutured to an appropriate blood source to be in fluid flow communication therewith and an opposed end of the graft is typically sutured to a side of the diseased vessel to be in fluid flow communication therewith downstream of the occlusion, or blockage. Another procedure involves suturing a side of a healthy vessel to a side of a diseased vessel downstream of the blockage, or occlusion, so that blood can flow from the healthy vessel to the diseased vessel. A joint between an end of a vessel, or graft, and a side of another vessel, or graft, is often referred to as an end-to-side anastomosis. A joint between a side of a graft, or vessel, and a side of another graft, or vessel, is often referred to as a side-to-side anastomosis.

During CABG surgery, a patient is often connected to a cardiopulmonary bypass machine so that the heart can be stopped temporarily, thereby to ease the task of suturing the various grafts, and/or vessels, together. Furthermore, blood vessels, such as the aorta, for example, are often closed, or clamped, so as to interrupt blood flow through that vessel when that vessel is to be used as a donor vessel or blood source.

When CABG procedures are performed on a patient, the patient normally suffers a great deal of trauma. Accordingly, it would be beneficial if such CABG procedures could be improved so as to decrease patient trauma. In conventional CABG surgery, there are at least three factors that affect the degree of trauma suffered by a patient. These factors include: (1) the time the patient spends on a cardiopulmonary bypass machine, (2) the time the patient spends with a clamped blood vessel, such as the aorta, or the like, and (3) the quality of the anastomoses formed between the blood vessels and/or grafts. It is generally recognized that the risk of patient morbidity rises significantly after the patient has been placed on a cardiopulmonary bypass machine for a period of about one hour. Passage of blood through a cardiopulmonary bypass machine tends to damage blood cells consequently causing degradation in blood quality. Accordingly, the longer a patient is subjected to cardiopulmonary bypass, the more the blood cells become damaged and the higher the degradation in the quality of the blood. A complication often associated with prolonged placement on a cardiopulmonary bypass machine, is distal thrombosis. Distal thrombosis can give rise to embolization in the neurovasculature and can lead to the patient suffering a stroke. Accordingly, it would be beneficial if the period a patient spends on a cardiopulmonary bypass machine during CABG surgery could be reduced.

A factor by which the amount of time a patient spends on a cardiopulmonary bypass machine can be reduced is by reducing the time taken suturing the vessels and/or grafts together to form anastomoses. The average time taken to suture two vessels together to form an anastomosis in accordance with traditional suturing methods, is typically about seven to ten minutes. An average CABG procedure can involve the formation of about five anastomoses. Accordingly, the time spent on suturing during an average CABG procedure can be between about thirty-five to fifty minutes. Therefore, since the task of suturing can constitute a major portion of the one hour period, it would be advantageous if the time spent on such suturing could be reduced. By doing so, the time a patient is subjected to cardiopulmonary bypass would also be reduced, thereby reducing patient trauma and the risks of morbidity.

In so-called "off-pump" procedures, patients are not placed on cardiopulmonary bypass machines. Accordingly, the negative effects associated with cardiopulmonary bypass mentioned above are inhibited. However, the task of suturing is made more difficult since the task of suturing is normally then performed while the heart is beating. This can lead to the formation of anastomoses with reduced integrity. Improperly suturing blood vessels and/or grafts together may lead to post operative complications. Incorrect suturing during surgery requiring correction during the surgery, may unnecessarily extend the time taken to complete the surgery.

Suture placement devices have been proposed which enable a surgeon, or the like, to place suture elements in patient tissue without manually holding and manipulating a suture needle, as has traditionally been the case. It has been found that the management of opposed ends of suture elements after having been placed in patient tissue with such a device can be rather tedious. This is especially true where the device is arranged to place a plurality of suture elements in patient tissue simultaneously. In such a case, opposed portions of each individual suture element are typically secured together to form a suture. It has been found that the opposed portions can become mixed up, or entangled, with one another, thereby unnecessarily complicating the suturing procedure and delaying its completion.

One such suture placement device is shown an described in U.S. patent application Ser. No. 09/784,704, filed Feb. 14, 2001 and entitled "Device and Method for Deploying and Organizing Sutures for Anastomotic and Other Attachments," the entirety of which is herein incorporated by reference.

Accordingly, it would be advantageous to provide systems, devices and methods for enabling suturing operations to be conducted with greater accuracy and in a shorter period of time. This is especially true if several vessels and/or grafts are to be sutured together during a CABG procedure.

SUMMARY OF THE INVENTION

According to one aspect of the invention, there is provided a suturing device including a suture guid and a needle holder. The suture guide includes a foot portion having an axis defined along a length of the foot portion. The foot portion includes a plurality of apertures, each aperture holding a suture. The needle holder movably holds at least one needle relative to a first side of the foot portion and movably holds at least one needle relative to a second side of the foot portion. The needles are movable into respective apertures, and the at least one needle on the first side of the foot portion is at an angle relative to the at least one needle on the second side of the foot portion. In another aspect of the invention, the device includes a body having a driving mechanism. At least one needle holder is adapted to be received by the body. The needle holder includes a plurality of needles wherein the needles are operatively coupled to the driving mechanism. The device may further include a suture holder having a first end and a second end. The first end is adapted to slidably engage the needle holder, and the second end further includes a plurality of apertures adapted to receive a plurality of sutures. The driving mechanism drives the needles into the second end of the suture holder at an angle relative to an axis extending along the first and second end of the suture holder.

DETAILED DESCRIPTION OF THE DRAWINGS

The objects and advantages of the invention will become apparent from the following detailed description of preferred embodiments thereof in connection with the accompanying drawings in which like numerals designate like elements in which.

DETAILED DESCRIPTION OF PREFERRED EMBODIMENTS

In accordance with the present invention there is shown and described a needle deployment device. The needle deployment device includes a main body having a driving mechanism therein. A pair of needle holder assemblies, wherein the needle holder assemblies include needles and needle guides. A suture holder having a first end and a second end, wherein the first end is operatively coupled to the driving mechanism and the second end is adapted to receive the needles, wherein the needles received sutures disposed within the suture holder.

Figure 1:
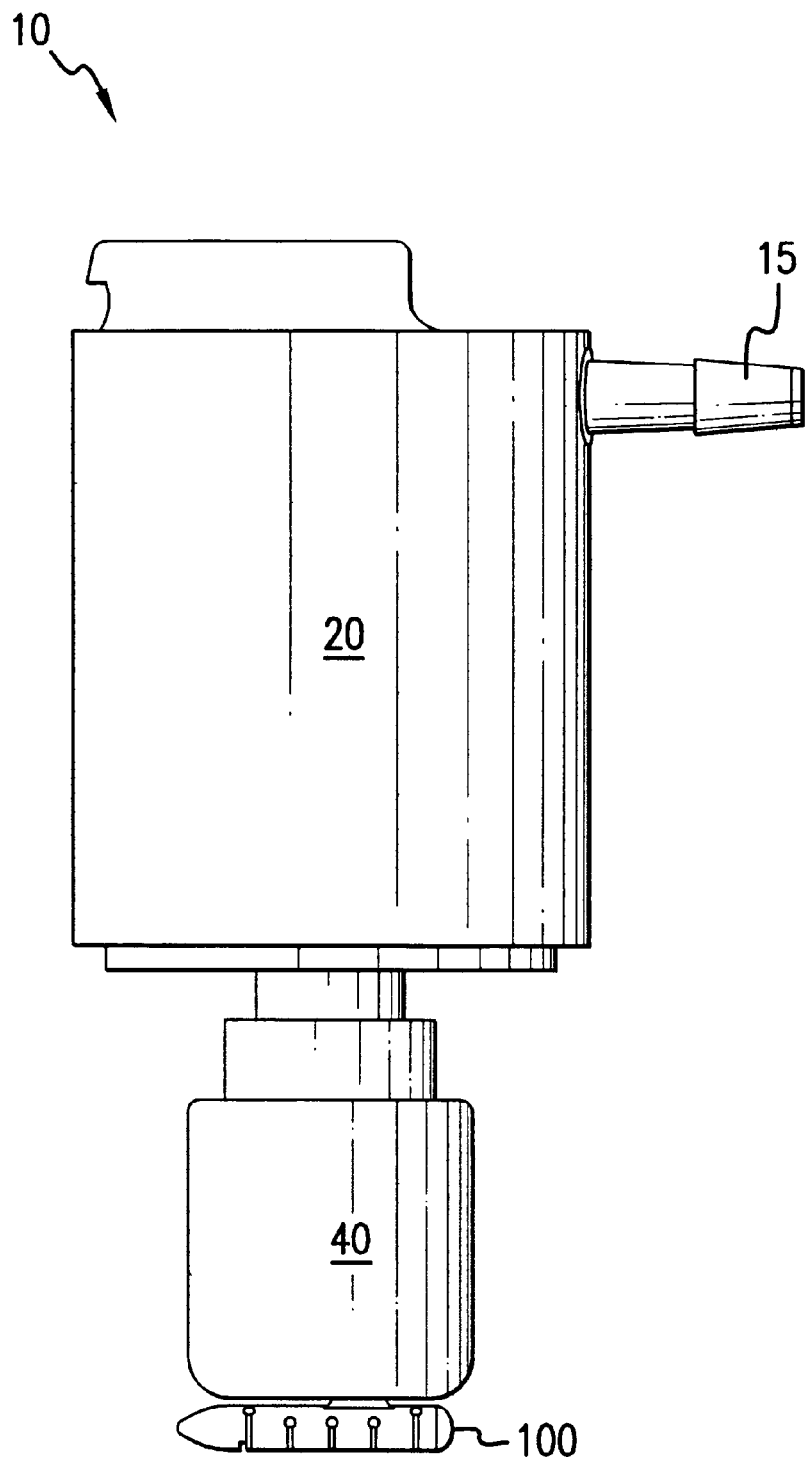
FIG. 1 is a side view of a needle deployment device in accordance with the present invention.

Referring now to FIG. 1 there is shown a representative embodiment of the needle deployment device 10 according to the present invention. The needle deployment device 10 includes a main body 20 including a fluid inlet 15 and a fluid outlet 16 (not shown), a needle holder assembly 40 and a suture holder 60. The needle deployment device 10 will be described in greater detail below with reference to FIGS. 1–15.

The main body 20 of the needle deployment device 10 may be constructed of any bio-compatible material such as titanium, stainless steel, or plastics. In a preferred embodiment, the main body 20 is constructed of plastic such as polyvinyl chloride or nylon or delrin.

The main body 20 may be constructed as a unitary body utilizing manufacturing processes such as injection molding or milling. Alternatively, the main body 20 may be constructed of multiple pieces which may then be assembled utilizing a bio-compatible adhesive. The main body 20 includes a chamber 22 wherein the fluid inlets 15 and the fluid outlet 16 are in fluid communication with the chamber 22. The chamber 22 is adapted to slidably receive a driving assembly 90. The driving assembly includes a wiper seal, a piston cap, a return spring, an end cap, a locking frame, and a drive shaft, each of which will be described in greater detail below with reference to FIGS. 2–14.

Figure 2:
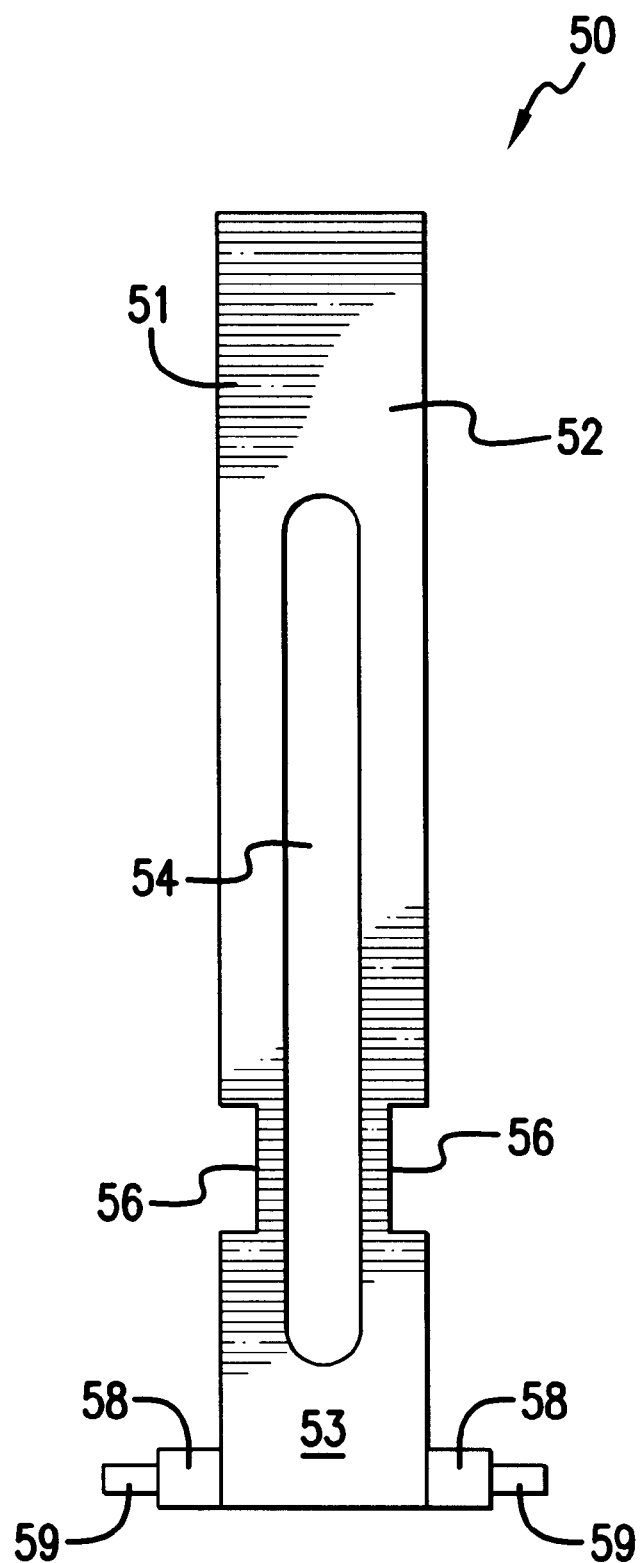
FIG. 2 is a side view of a drive shaft of the needle deployment device in accordance with the present invention.

Referring now to FIG. 2 there is shown the drive shaft 50 of the driving assembly 90. The drive shaft 50 comprises an elongated body 52 having a proximal end portion 51 and distal end portion 53, a first slot 54, grooves 56, projections 58, and pins 59 extending from the projections 58. The proximal end portion 51 of the drive shaft is adapted to be fixedly attached to the wiper seal 95 of the driving assembly 90. The drive shaft 50 may be constructed as a unitary member of may be constructed of multiple parts which may then be assembled.

The drive shaft may be constructed of bio-compatible materials such as titanium, stainless steel, or plastics. Preferably, the drive shaft 50 is constructed of a bio-compatible plastic such as delrin or nylon.

Figure 3:
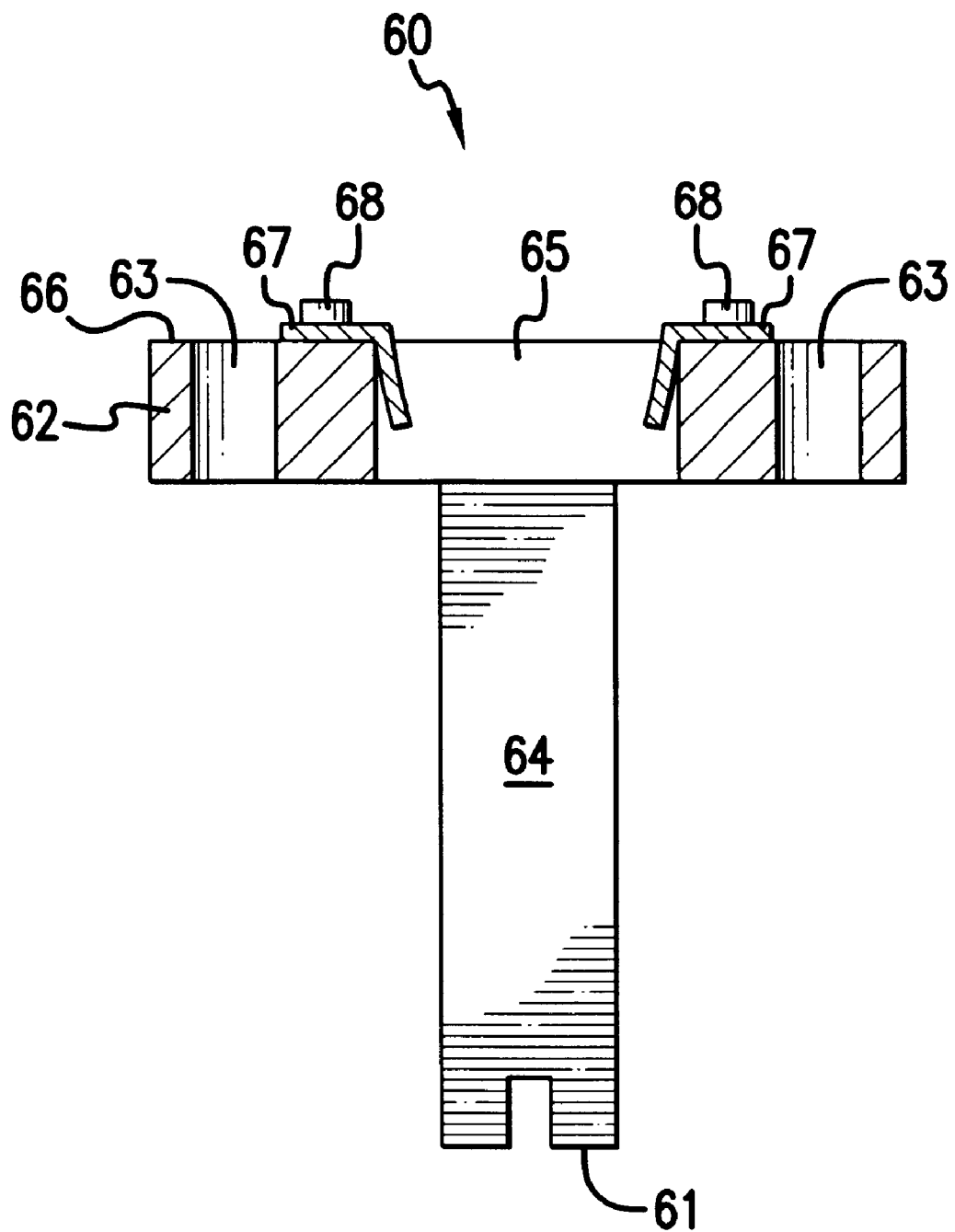
FIG. 3 is a side view of a locking body of the needle deployment device in accordance with the present invention.

Referring now to FIG. 3 there is shown the locking frame 60 of the driving assembly 90. The locking frame includes a body 62, wherein the body 62 includes a first projection 64 and a second projection 64' (not shown). The body 62 further includes a plurality of apertures 63 and 65 disposed therethrough. The apertures 63 are adapted to receive and retain a tab disposed upon the needle guide assembly as will be described in greater detail below. Additionally, the locking frame further includes biasing members 67. The biasing members 67 are fixedly attached to a first side 66 of the body 62 of the locking frame 60 and extend into the aperture 65 of the locking frame 60. The distal end portion 61 of the first and second projections is adapted to receive the needle guide assembly as will be described in greater detail below.

The locking frame may be constructed of bio-compatible materials such as stainless steel, titanium or plastics. In a preferred embodiment the locking frame 60 is constructed of nylon. The locking frame may be constructed utilizing known manufacturing processes such as machining or injection molding. The biasing members 67 may be constructed of a bio-compatible material such as stainless steel, titanium or plastics. In a preferred embodiment the biasing members 67 are constructed of a nickel-titanium alloy Nitinol. In accordance with the present invention the biasing members 67 may be integrally formed with the locking frame 60.

As previously noted, the needle deployment device 10 includes guide assemblies 40, wherein the guide assemblies 40 will be described in greater detail below with reference to FIGS. 4 through 7.

Figure 4:
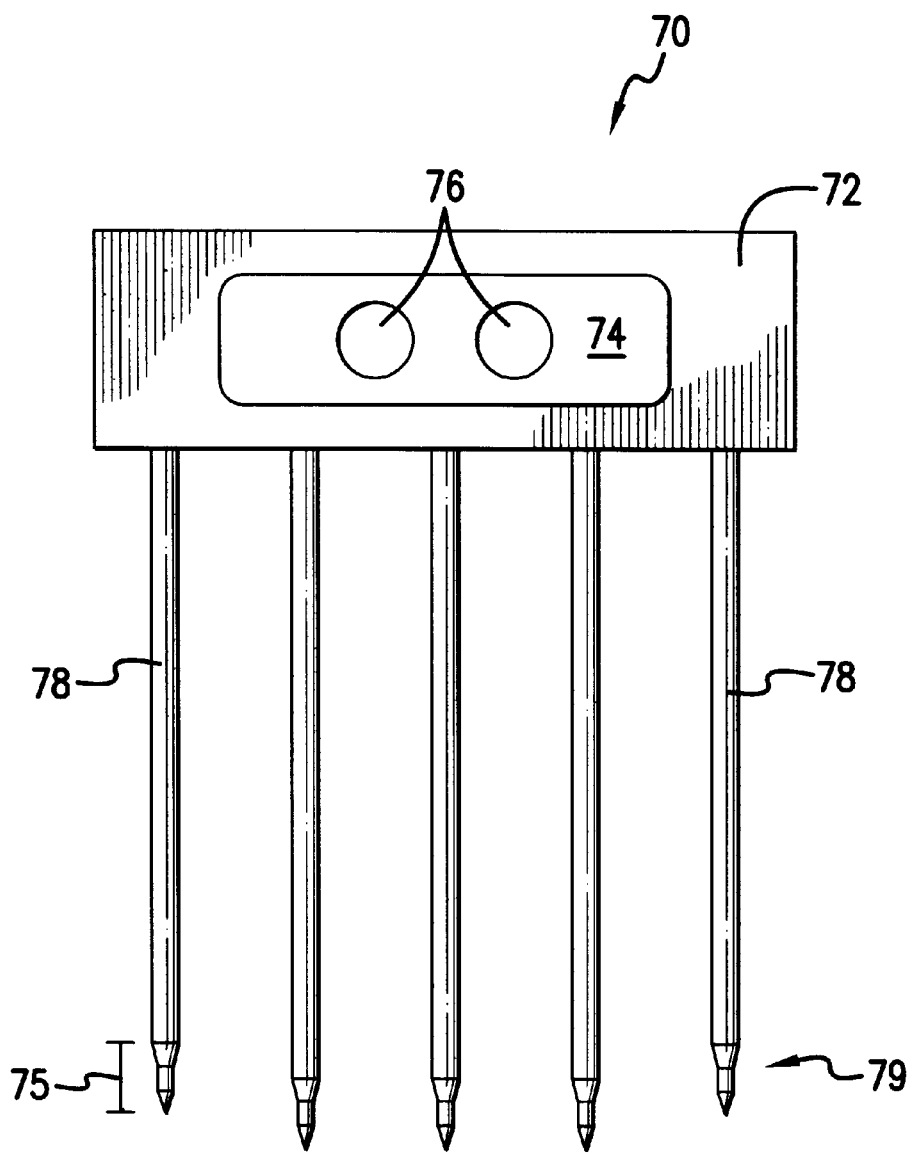
FIG. 4 is a side view of a needle block assembly of the needle deployment device in accordance with the present invention.

Referring now to FIG. 4 there is shown a guide assembly 40 in accordance with the present invention. The guide assembly 40 includes a needle block assembly 70 having a plurality of needles 78, and a core 80. The needles 78 include a distal end portion 77 (not shown) and a proximal end portion 79, wherein the distal end portion 77 is adapted to be received within apertures 73 formed within the needle block 72. The proximal end portion 79 of the needles 78 contain a reduced cross-sectional area 75 as shown in FIG. 4. The needles 78 extend from the needle block 72, wherein the outer needles do not extend from the needle block 72 as far as the inner needles.

The needle block 72 further includes a chamber 74 and at least one aperture 76 disposed therethrough, wherein the chamber 74 and aperture 76 are disposed about an axis perpendicular to an axis which the needles 78 extend along. Furthermore, the aperture 76 is adapted to receive the pins 59 extending from the projections 58 of the drive shaft 50 as will be described in greater detail below.

The needle block 72 may be constructed of bio-compatible materials such as titanium, stainless steel, Nitinol, or plastics. In a preferred embodiment the needle block 72 is constructed of nylon. The needles 78 may be constructed of bio-compatible materials such as stainless steel or titanium. In a preferred embodiment the needles are constructed of a nickel-titanium composite (Nitinol). Additionally, the needles are constructed wherein the needles are sufficiently resilient and are capable of being readily deformed. The needles in a preferred embodiment have a round cross-sectional profile, though it is contemplated that the needles may have other cross-sectional profiles. For example, the needles may have a square, rectangular, oval or similar cross-sectional profile.

As discussed above the distal end portion of the needles are fixedly attached within the apertures 73 of the needle block 72. The needles may be fixedly attached within the apertures 73 using bio-compatible adhesives. Alternatively, the needles 78 may be inserted within the molding process if the needle block 72 is molded. Still further, it is contemplated that other methods may be utilized to affix the needles within the needle block 72, for example, the needles may be fixed within the needle block by melting the needle block.

As previously noted, the needle deployment device 10 of the present invention includes a plurality of guide assemblies 40. The guide assemblies 40 include a housing, a core, and a needle block assembly wherein the needle block assembly includes a plurality of flexible needles. The guide assemblies 40 will be described in greater detail with reference to the FIGS. 5–8.

Figure 5:
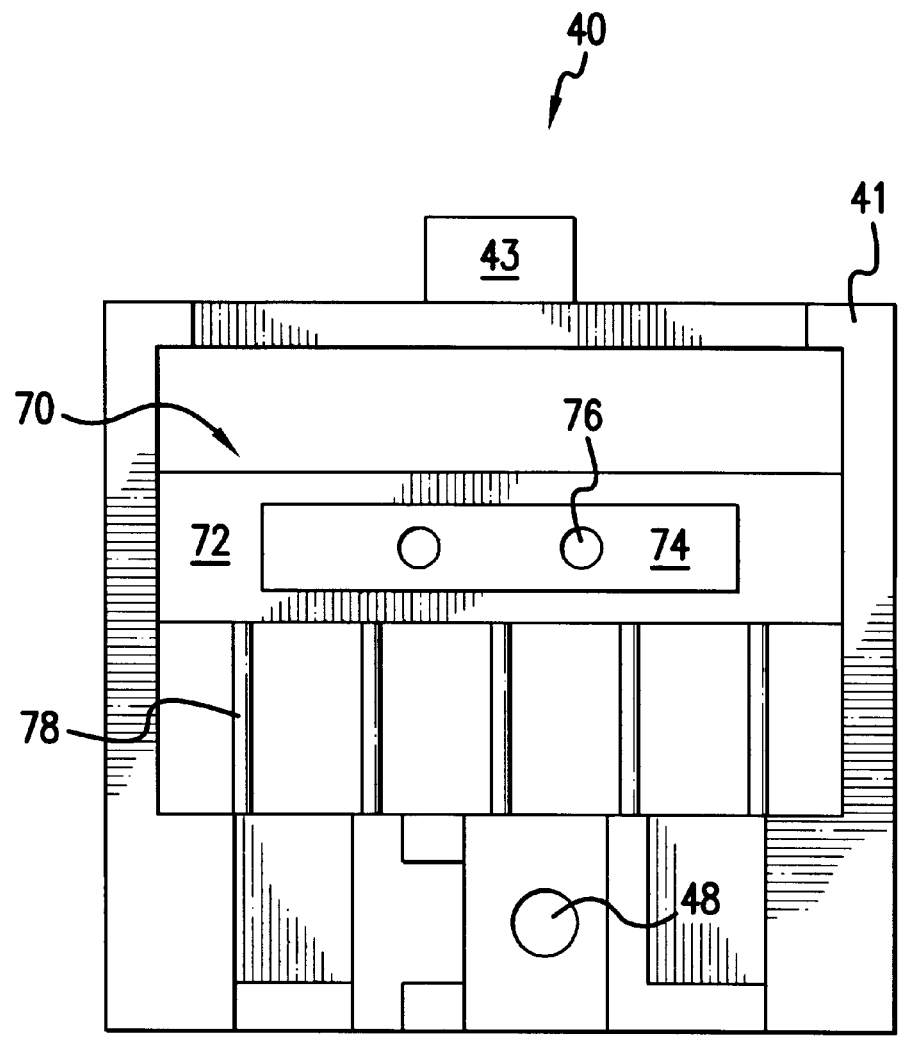
FIG. 5 is a side view of a guide assembly of the needle deployment device in accordance with the present invention.

Referring now to FIG. 5, there is shown a front view of a guide assembly 40, wherein the guide assembly 40 includes a housing 41, a biasing member 47 (not shown), a locking pin 48, and a needle block 80. A detailed description is provided below with reference to a single guide assembly 40, wherein it shall be understood that the second guide assembly in a preferred embodiment is a mirror image thereof, excluding the biasing member and locking pin of the first guide assembly wherein the second guide assembly is adapted to receive the locking pin projecting from the first guide assembly.

Figure 7:
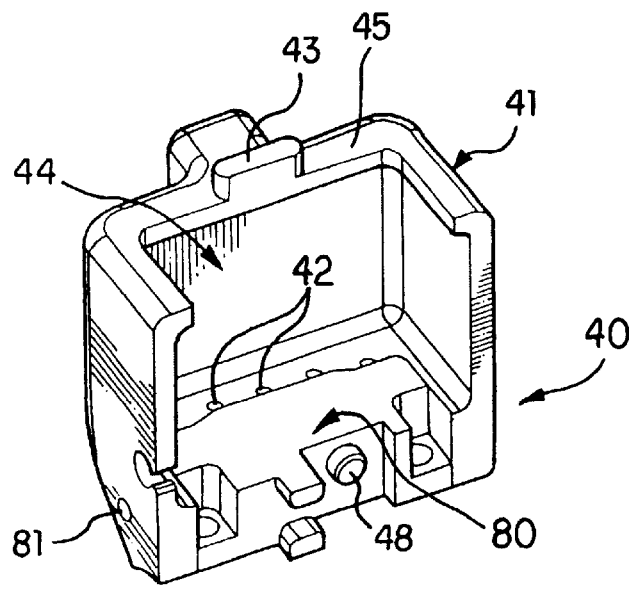
FIG. 7 is an isometric front view of the guide assembly of the needle deployment device in accordance with the present invention.
Figure 6:
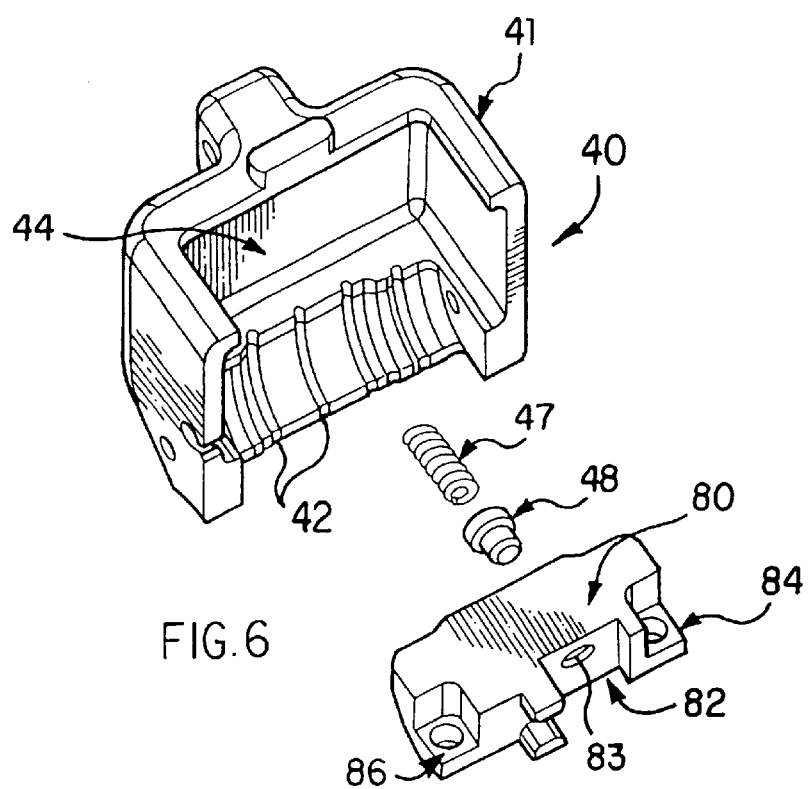
FIG. 6 is an isometric expanded front view of the guide assembly of the needle deployment device in accordance with the present invention.

Referring now to FIGS. 6 and 7 there are shown an expanded view and an assembled isometric view of the guide assembly 40 in accordance with the present invention, wherein the guide assembly 40 and the core 80 have been assembled within the body 41 of the guide assembly 40. A needle block assembly 70 (not shown), as described in detail above, may be slidably disposed within the chamber 44 of the body 41 of the guide assembly 40. The needles 78 are adapted to be received within a plurality of needle guides 50, as will be described in greater detail below. The core 80 as assembled within the body 41 of the guide assembly 40 retains the biasing member 47 and the locking pin 48, wherein the locking pin 48 may be biased between a retracted position and an extended position.

Referring now to FIG. 6 and the core 80 shown therein. The core 80 further includes a recessed area 82 and an aperture 83 wherein the aperture 83 is adapted to slidably receive the locking pin 48 therein. The core 80 further includes a first cavity 84 and a second cavity 86, wherein the first cavity 84 and the second cavity 86 are adapted to receive the distal end portion 61 of the locking frame 60 as will be described in greater detail below.

Referring now to FIG. 7, there is shown an isometric view of the guide assembly 40 according to the present invention. As shown in FIG. 7, the body 41 of the guide assembly 40 further includes a tab 43 projecting from the proximal end portion 45 of the body 41. The tab 43 is adapted to be received within the locking frame 60 as will be described in greater detail below. In addition, the body 41 is adapted to slidably receive the needle block assembly 70, wherein the needles 78 are slidably received within the needle guides 50. As shown in FIG. 6, the needle guides are adapted to direct the flexible needles 78 at an angle relative to the direction of motion of the needle block assembly. The function of the needle guides will be described in greater detail below.

The core 80, body 41 and locking pin 48 may be constructed of bio-compatible materials such as titanium, stainless steel, or plastics. In a preferred embodiment, the core 80 and body 41 are constructed of plastic. In a preferred embodiment, the locking pin 48 is constructed of stainless steel. The core 80 and body 41 may be constructed using known manufacturing methods such as machining or injection molding. In a preferred embodiment, the core 80 and body 41 are constructed using injection molding. The locking pin 48 may be constructed using any of the methods described above, in a preferred embodiment the locking pin 48 is machined.

The core 80 may be secured to the body 41 using a plurality of pins 81 as shown in FIG. 7. Alternatively, in accordance with the present invention, the core may be fixedly attached to the body using a bio-compatible adhesive. In accordance with the present invention, the core and body may be integrally formed wherein the needle guides are formed therein during the manufacturing process.

Figure 8:
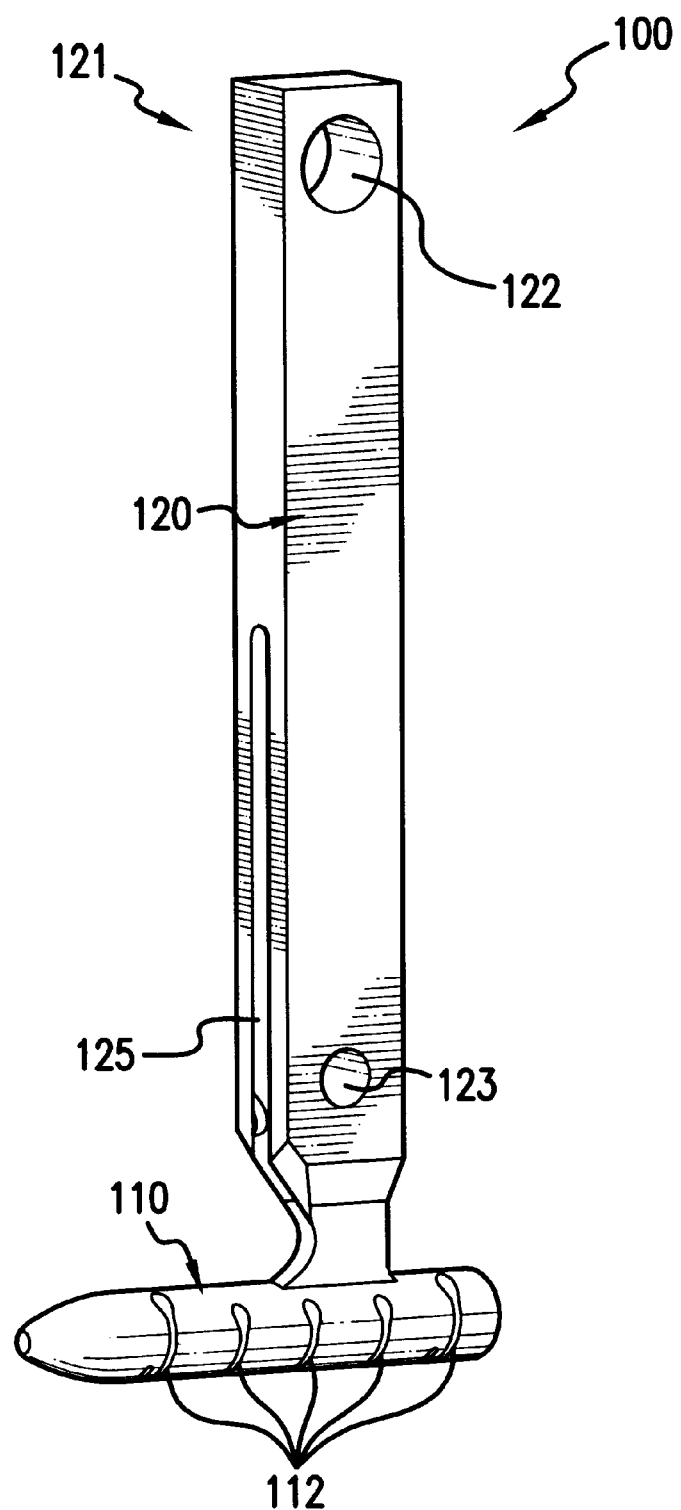
FIG. 8 is a isometric side view of the suture guide of the needle deployment device in accordance with the present invention.
Figure 13:
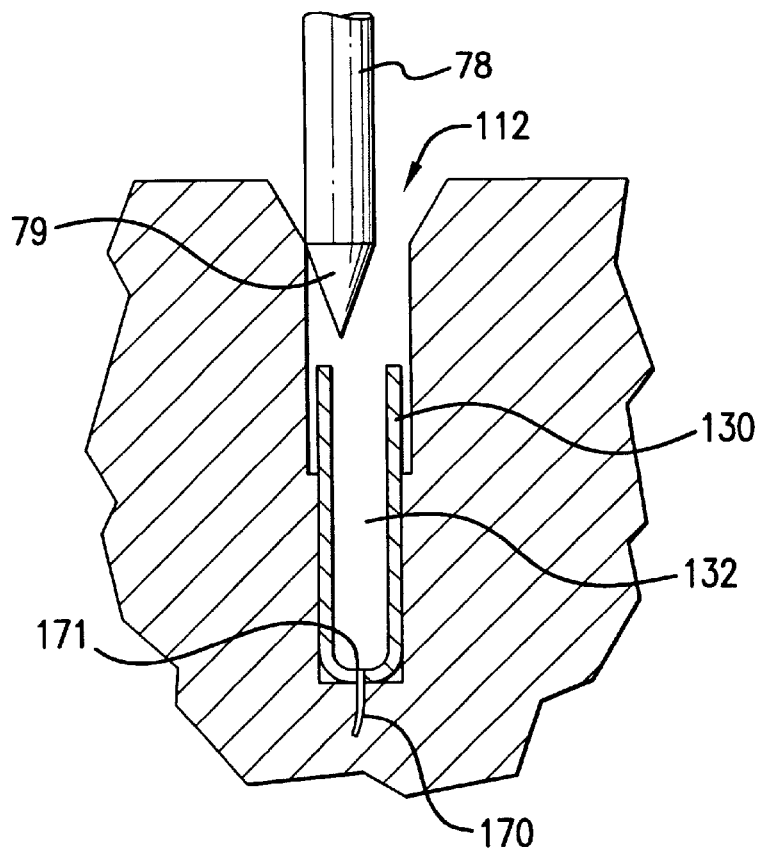
FIG. 13 is a cross-sectional side view of the foot of the suture guide illustrating the cuff and suture disposed therein.

Referring now to FIG. 8 there is shown the suture guide 100 in accordance with the present invention. The suture guide 100 includes a foot portion 110 and a shaft portion 120. The shaft portion 120 of the suture guide 100 includes an aperture 122 disposed therethrough adjacent a proximal end portion 121 and a second aperture 123 disposed adjacent the foot 110. Additionally, the shaft portion 120 further includes a groove 125 disposed therein adjacent the foot portion 110 of the suture guide 100, wherein the groove 125 is adapted to receive a suture hook 150 (shown in FIG. 10). The foot 110 of the suture guide 100 further includes a plurality of a suture holders 112, wherein the suture holders 112 are adapted to receive cuffs 130 as shown in FIG. 13. The cuffs 130 are fixedly attached to suture 170, wherein the suture is guided through a suture guide 113 of the foot 110. Additionally, the cuffs 130 are further adapted to receive the proximal ends 79 of the needles, wherein the proximal ends 79 of the needles 78 engage the cuffs 130 as will be described in greater detail below with reference to FIGS. 15A through 15D.

Figure 10:
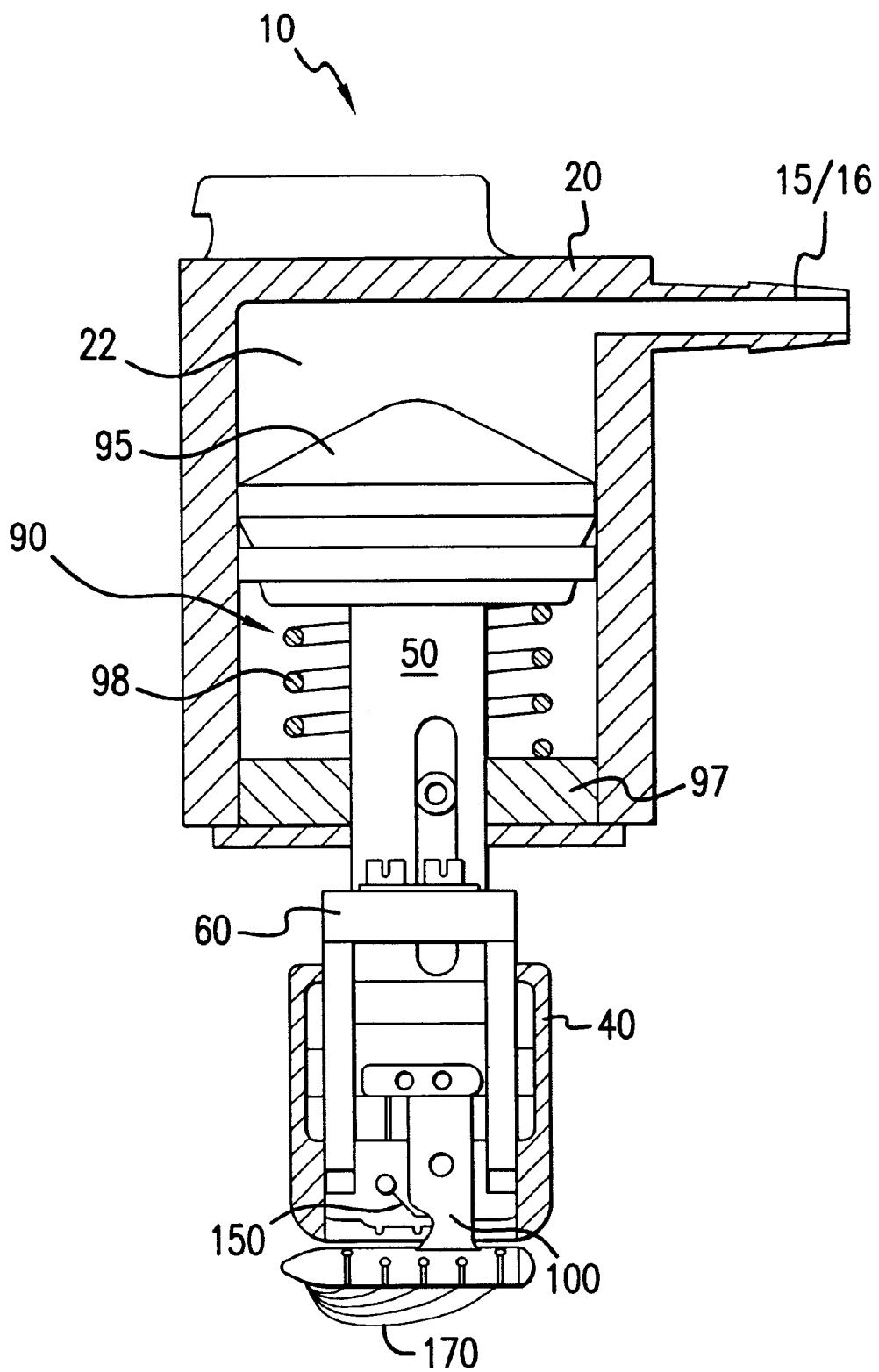
FIG. 10 is a cross-sectional side view of the needle deployment device in accordance with the present invention.
Figure 11:
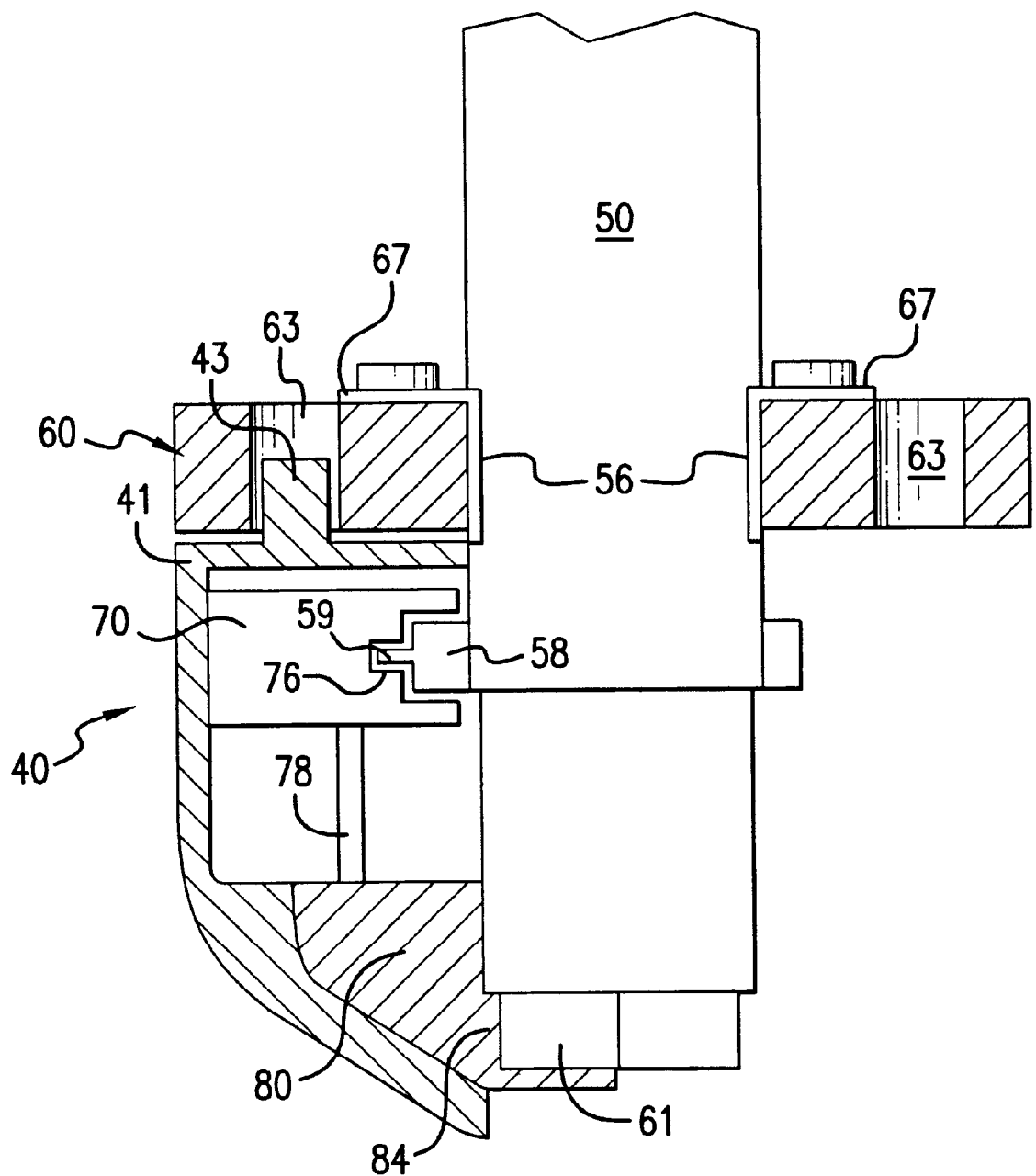
FIG. 11 is a partial cross-sectional side view of the distal end portion of the needle deployment device in accordance with the present invention illustrating the guide assembly installed thereupon.
Figure 12:
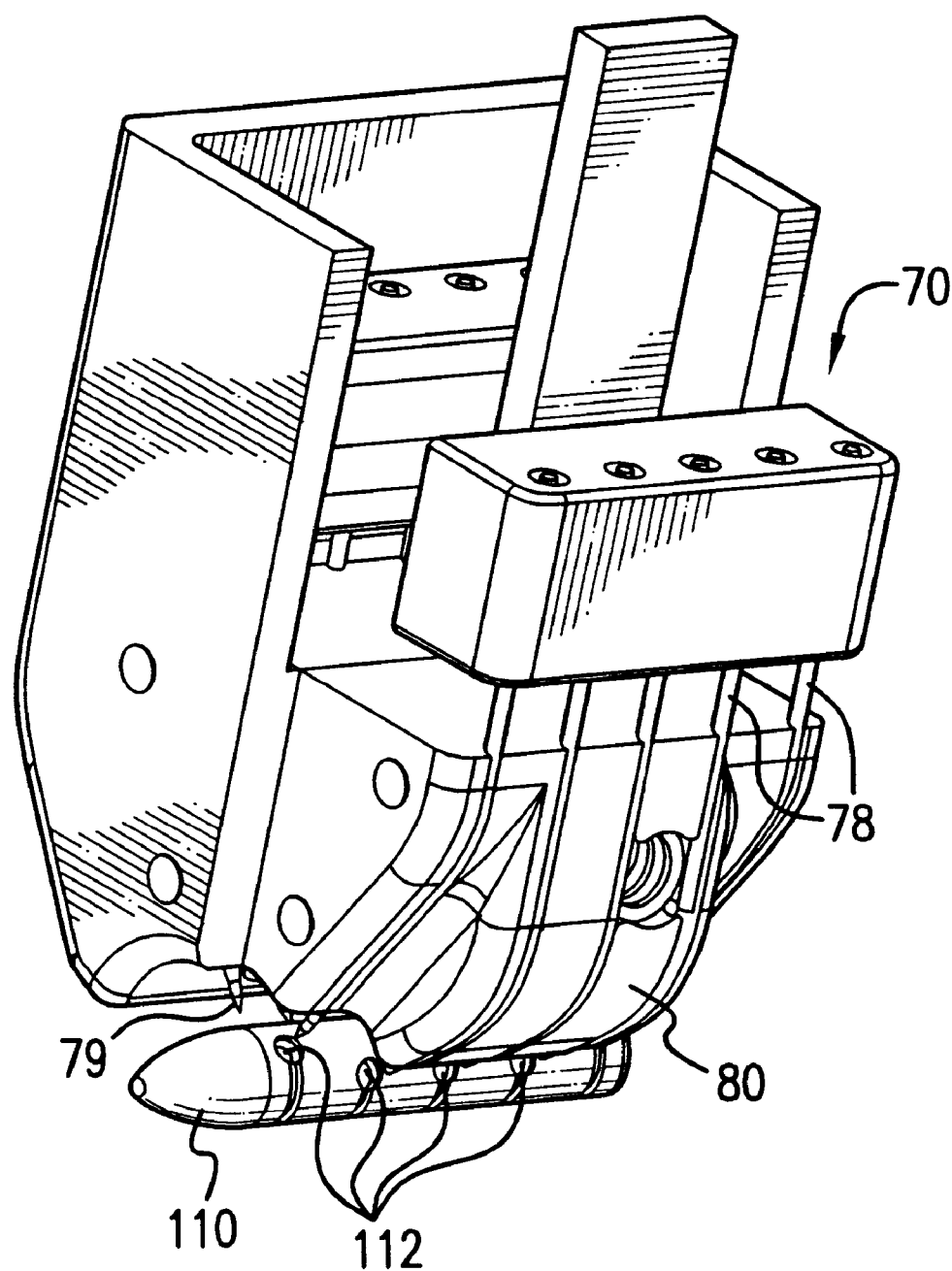
FIG. 12 is an isometric partial cut-away view of the guide assembly of the needle deployment device in accordance with the present invention.

Referring now to FIGS. 10–12, there are shown partial cross-sectional views or cut-away views of the needle delivery device 10 as assembled. Referring now to FIG. 10, there is shown a cross-sectional side view of the needle delivery device 10 in accordance with the present invention. As shown in FIG. 10, the driving assembly 90 is disposed within the chamber 22 of the main body 20. The wiper seal 95 sealingly engages the wall of the chamber 22, thereby providing a fluid tight seal between the chamber and the proximal end of the wiper seal 95. The end cap 97 is disposed at the distal end of the chamber 22, whereby the end cap 97 may be fixedly attached to the main body 20 with a bio-compatible glue or alternatively, the end cap 97 may be removably attached to the main body 20 through the use of mechanical fasteners or molded fasteners.

The wiper seal 95 may be constructed of a suitable pliable material such as rubber, silicone, urethane or preferably of polyisoprene. The piston cap (not shown), end cap 97, drive shaft 50, and locking frame 60 may be constructed of a bio compatible material such as titanium, stainless steel, or plastics, preferably they are constructed of polycarbonate according to known manufacturing methods such as injection molding or machining. The return spring 98 and locking tabs 67 are preferably constructed of stainless steel, though it is contemplated that other bio-compatible materials may be utilized.

As fluid force acts on the proximal end of the wiper seal 95, the driving assembly 90 is advanced within the chamber 22 of the main body 20, thereby advancing the locking frame along the length of the drive shaft 50. At least one locking tab 67 disposed upon the locking frame 60 is received within a slot 56 on the drive shaft 50 as shown in FIG. 11. After the locking tab 67 has engaged the drive shaft 50 as shown in FIG. 11, the guide assembly 40 can no longer advance along the length of the drive shaft 50. At this point, the guide assembly 40 is positioned at a pre-determined height above the vessel wall for deployment of the needles. After the guide assembly 40 engages the drive shaft 50 as described above, further force acting on the driving assembly 90 causes the drive shaft 50 to advance the needles 78. The needles are operatively coupled to the drive shaft 50 through pins 59 extending from the projections 58 of the drive shaft 50 which are disposed within the aperture 76 of the needle block assembly 70 as shown in FIG. 11.

As shown in FIG. 1 the tab 43 disposed on the proximal end portion of the body 41 of the guide assembly 40 is received within the aperture 63 of the locking frame 60 and the distal end portion 61 of the locking frame 60 is received within the first chamber 84 of the core 80, thereby removably attaching the guide assembly to the distal end portion of the needle deployment device 10.

Figure 14:
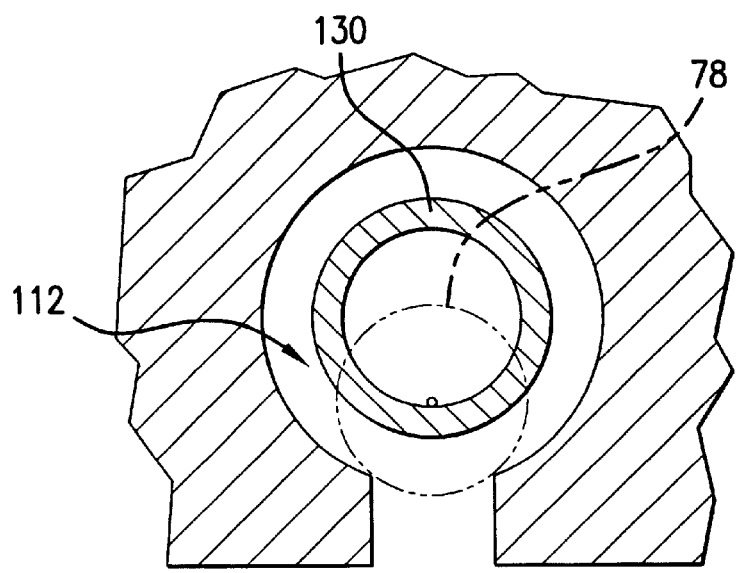
FIG. 14 is a top view of the foot of the suture guide illustrating the cuff disposed therein.

Referring now to FIG. 12, there is shown a cut-away isometric view of the distal end portion of the needle deployment device 10. As shown in FIG. 12, the core 80 is adapted to guide the needles 78 such that the proximal end portion 79 of the needles 78 are received within the cuff holders 112 of the foot 110. Referring now to FIGS. 13 and 14 there are shown a side view and a top view of the proximal end portion 79 of the needle 78 as received within the cuff holder 112 and cuff 130. As shown, the proximal portion of the cuff holder 112 is adapted to direct the proximal end portion 79 of the needle 78 towards the chamber 132 of the cuff 130. Therefore, when the needles 78 are driven into the cuff holders 130 the cuff holders 112 will ensure that the proximal end portion 79 of the needles are received within the chamber 132 of the cuff 130, thus ensuring capture of the cuffs 130 by the needles 78. Furthermore, this feature allows for greater manufacturing tolerances as well as for variables which are unforseen during use. For example, if a needle is slightly deflected due to plaque buildup within a vessel, the proximal portion of the cuff holder 130 will ensure that the needle 78 will be received within the cuff 130 for capture.

Figure 9:
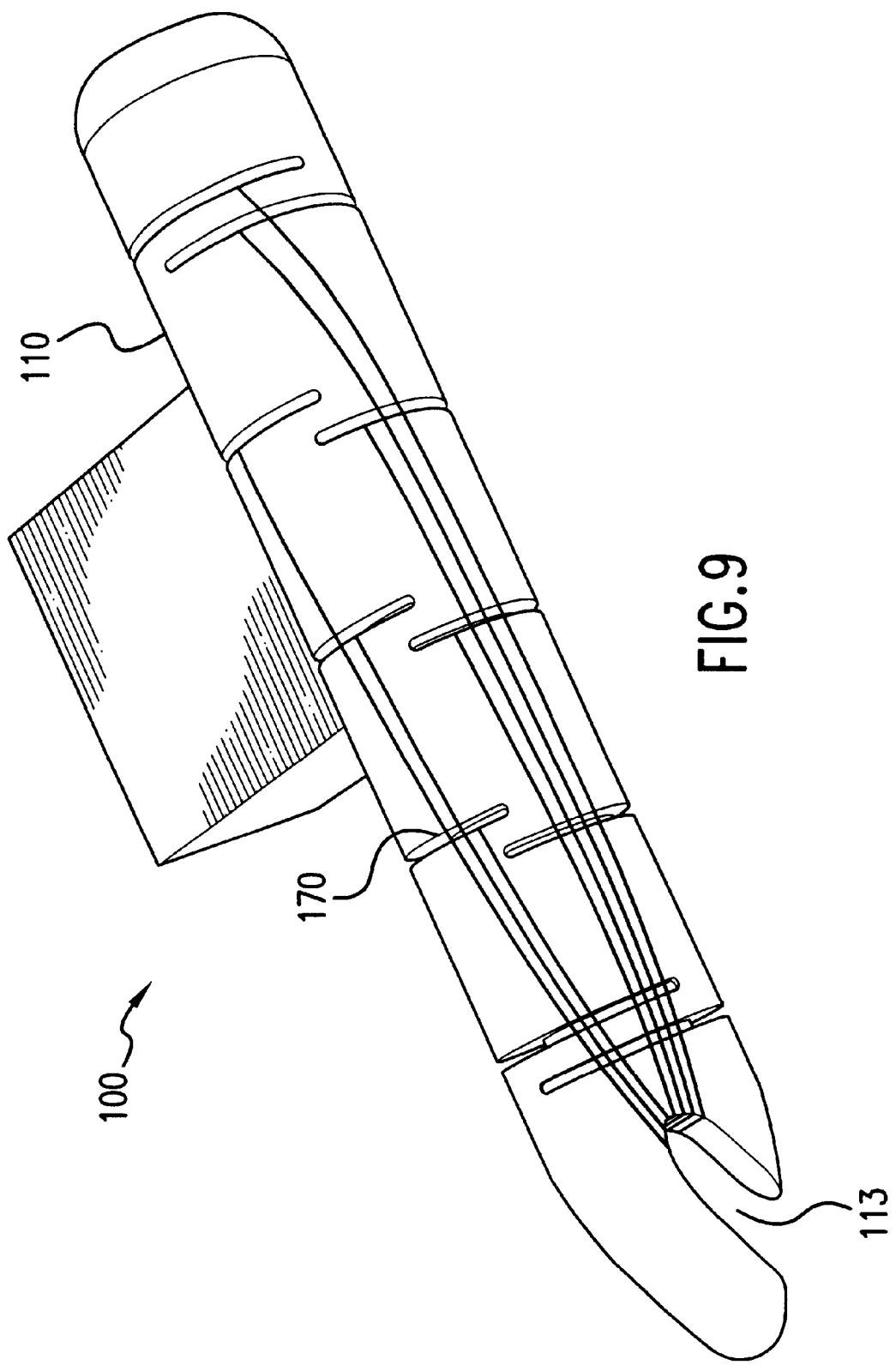
FIG. 9 is an isometric bottom view of the suture guide of the needle deployment device in accordance with the present invention.

The cuffs 130 may be manufactured of a bio-compatible material such as titanium, stainless steel, or plastics. The cuffs 130 have a generally cylindrical cross-sectional profile with an aperture disposed therethrough. The proximal end portion of the cuff 130 is adapted to receive the proximal end portion 79 of the needle 78. The distal end portion of the cuff 130 is adapted to receive suture 170, wherein the suture may be fixedly attached within the aperture 171 of the cuff with a bio-compatible adhesive, fusing the cuff with the suture, crimping the cuff, or similar methods of attachment. The suture may be any one of the known sutures available from various suppliers and known to one skilled in the art. As shown in FIG. 9, the suture S extending from the distal end of the cuffs is gathered and arranged to run along the distal surface of the foot 110 from the distal end portion through a suture channel 113 disposed within the proximal end portion of the foot 110. The suture S then extends along the elongated shaft within the groove of the suture holder 100, wherein the suture hook 150 retains the suture within the groove as shown in FIG. 10. The suture hook 150 may be constructed of bio-compatible materials such as stainless steel, titanium or Nitinol.

Figure 15A:
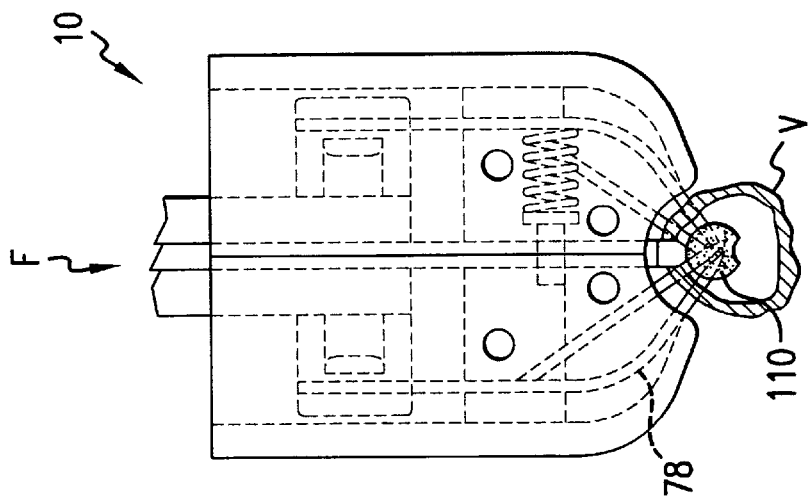
FIG. 15A is a side view illustrating the distal end of the needle deployment device in accordance with the present invention disposed within a vessel prior to use.
Figure 15B:
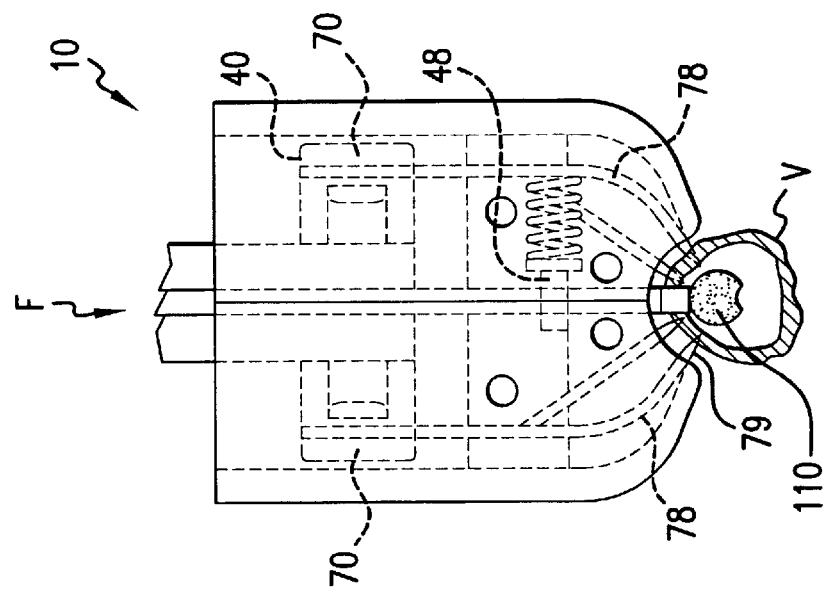
FIG. 15B is a side view illustrating the distal end of the needle deployment device in accordance with the present invention disposed within a vessel wherein the needles have been deployed.
Figure 15C:
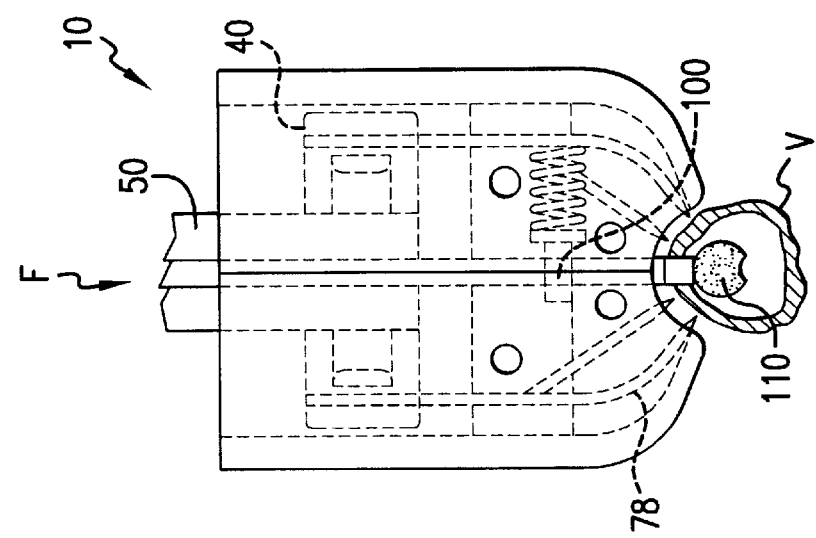
FIG. 15C is a side view illustrating the distal end of the needle deployment device in accordance with the present invention disposed within a vessel wherein the needles have been received within the cuffs of the device.

In accordance with the present invention, referring now to FIGS. 15A–15D there is shown in sequence the needle deployment device 10 in use. Referring now to FIG. 15A there is shown a partial front view of the needle deployment device 10, wherein the distal end portion of the needle deployment device has been inserted into a vessel. A fluid force F is applied to the drive shaft 50 by applying force to a fluid source that is operatively coupled to the chamber 22 of the main body 20, wherein the fluid force F acts upon the driving assembly 90 as described above. In response to the fluid force F applied to the driving assembly 90, the guide assemblies 40 are driven along the length of the suture guide 100 until the locking tabs 67 are received within a recessed area 56 of the drive shaft 50, whereby the locking tabs 67 prevent further motion of the guide assemblies 40 as well as placing the guide assemblies 40 at a pre-determined height above the surface of the vessel in which the needles are to be deployed. Referring now to FIG. 15B, wherein the guide assemblies 40 have become locked, the force F subsequently drives the needle block assemblies 70 and needles 78 through the vessel wall V, wherein the proximal end 79 of the needles 78 are received within the cuffs 130 of the foot 110 as shown in FIG. 15C. The needles are driven in a predetermined path defined by the needle guides within the body and core of the needle assembly. The path which the needles are driven along is at an angle relative to a vertical axis of the foot 110. The curved needle path allows for greater tissue capture during deployment of the device. The term tissue capture shall be understood as the amount of tissue between the incision through which the foot has been placed and the location within the vessel wall where the needles enter. The needle deployment device exhibits good tissue capture because the needles are driven through the vessel wall at a distance from the incision through which the foot is placed.

Figure 15E:
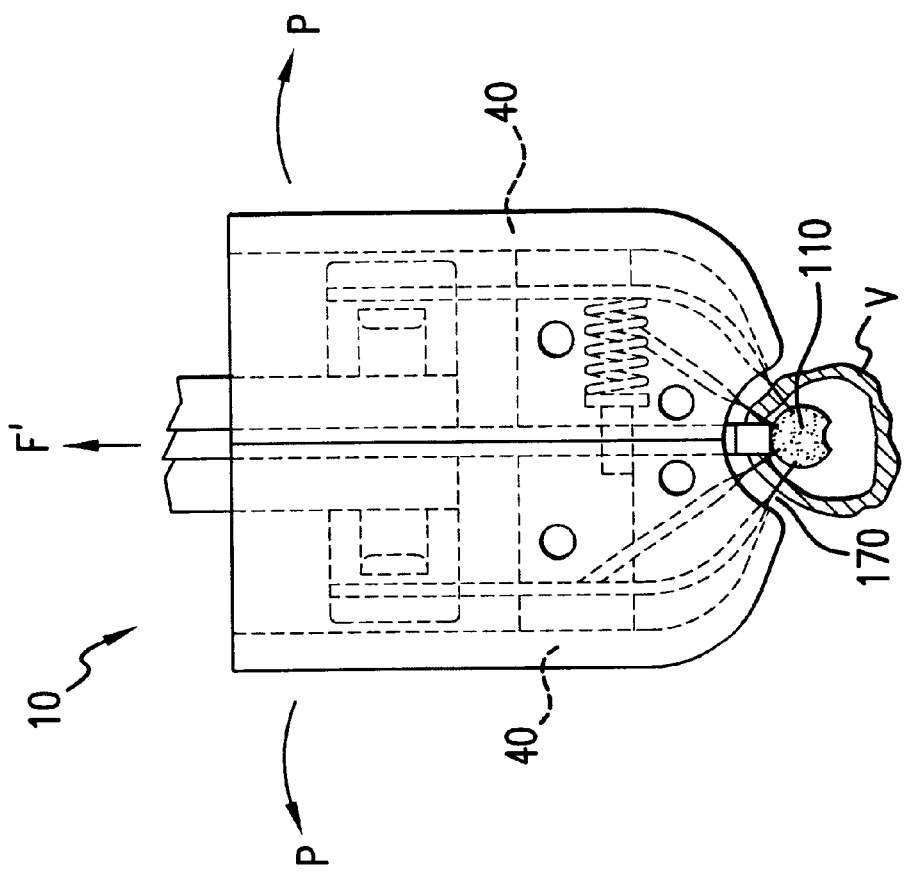
FIG. 15E is a side view illustrating the distal end of the needle deployment device in accordance with the present invention disposed within a vessel wherein the needles have been fully retracted and the suture has been drawn through the vessel wall.
Figure 15D:
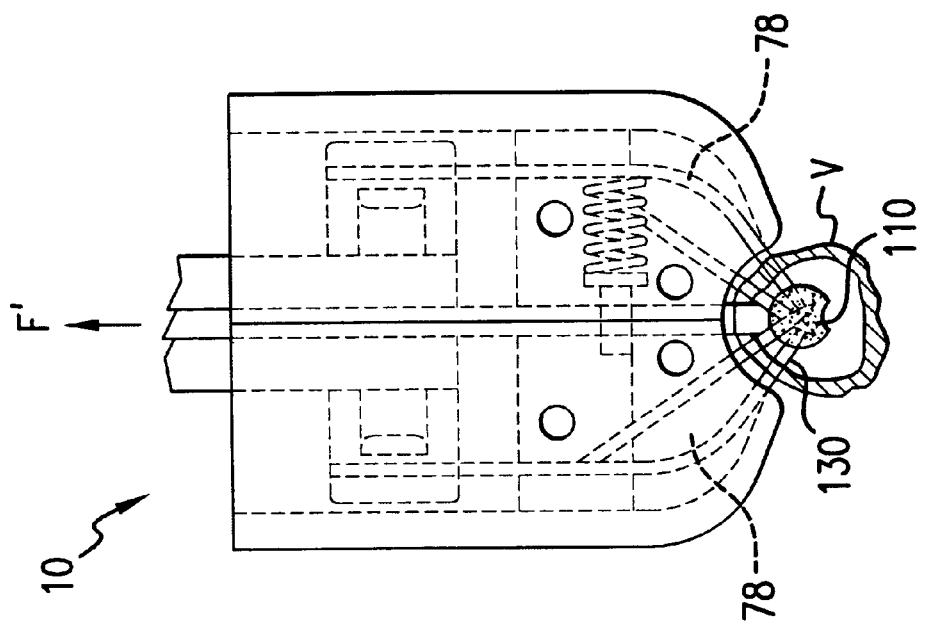
FIG. 15D is a side view illustrating the distal end of the needle deployment device in accordance with the present invention disposed within a vessel wherein the needles have been partially retracted thereby withdrawing the cuffs from the suture guide.

After the proximal ends 79 of the needles 78 have been received within the needle cuffs 130 as shown in FIG. 15D, a vacuum force is applied to the chamber 22 of the main body 20, wherein the vacuum and return spring act to withdraw the needles from the foot 110 and through the vessel wall as shown in FIG. 15E. As described in detail above, the foot is adapted to receive and align the proximal end portion of the needles such that the needles are axially received within the cuff 130. As the needles are retracted into the guide assemblies 40, the suture 170 previously retained within the suture track 113 on the foot 110 of the needle deployment device 10 is drawn through the vessel wall V.

After the needles have been fully retracted within the guide assemblies 40, the guide assemblies 40 may be removed from the distal end portion of the needle deployment device 10 and the foot may be removed from the vessel.

Figure 16:
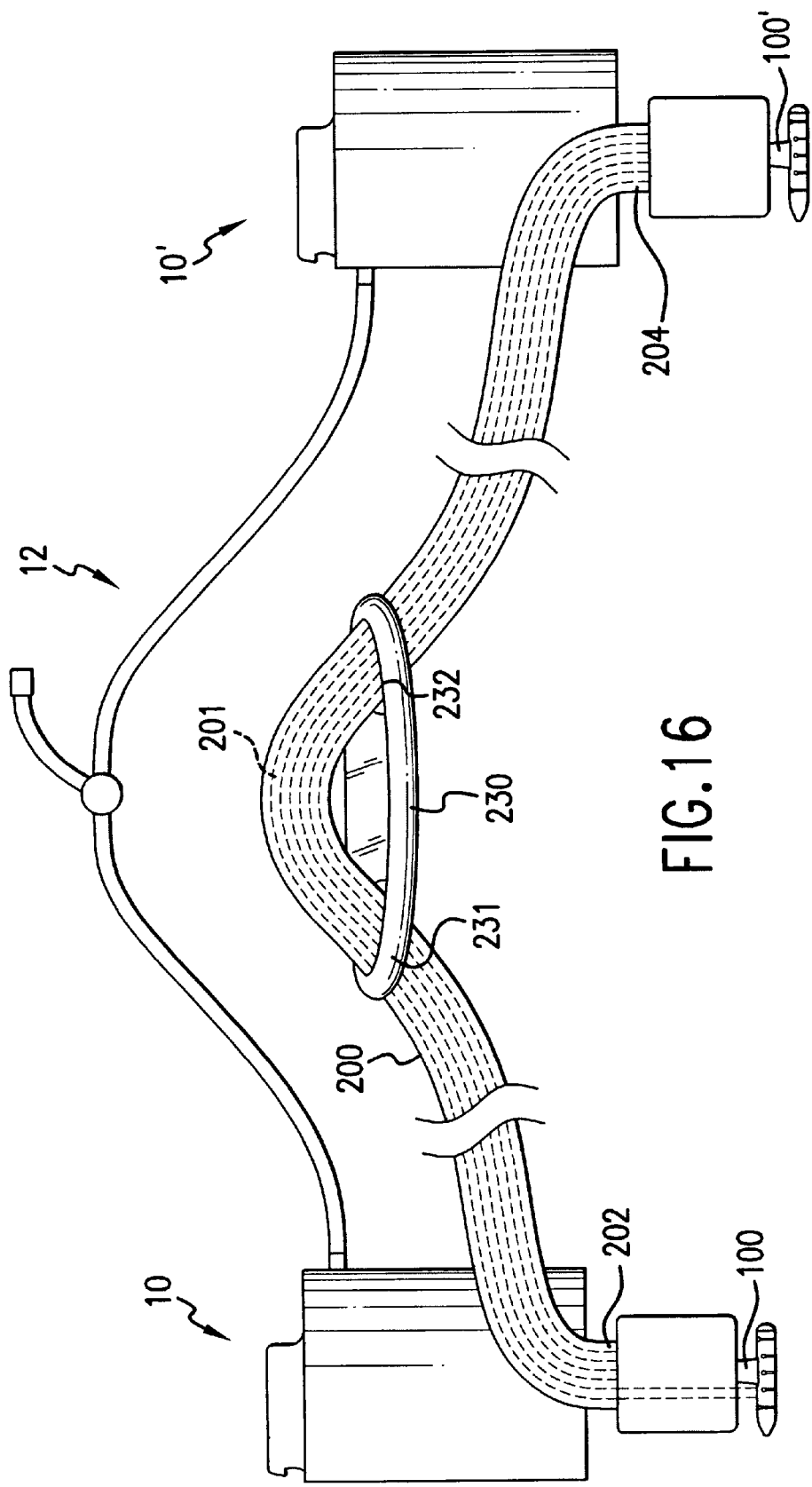
FIG. 16 is a side view of a system for performing side to side anastomoses utilizing the needle deployment device according to the present invention.

Referring now to FIG. 16 there is shown an anastomosis assembly 15, the assembly includes a first needle deployment device 10 connected with a second needle deployment device 10'. As shown in FIG. 16 the two needle deployment devices 10 and 10' are connected with a flexible belt 200. The flexible belt 200 includes at least one lumen extending therethrough, wherein a first end 202 of the belt 200 is connected to the first needle deployment device 10 and the second end 204 of the belt is connected to the second needle deployment device 10'. A first end of the suture 270 extends from the suture support 100 of the first needle deployment device 10, through the lumen of the belt 200 to the suture support 100' of the second needle deployment device 10' as shown. As shown in FIG. 16, the belt may further include a buckle 230 as shown, wherein the buckle 230 includes a first aperture 231 and a second aperture 232 wherein the belt is threaded therethrough, and the buckle 230 being slidably disposed upon the belt 200.

The anastomosis assembly 15 is suitable for performing side to side anastomosis between two vessels, wherein the first needle deployment device 10 and the second needle deployment device 10' are inserted into a first and second vessel respectively. After each of the devices have been deployed as described in detail above, the belt is opened, thereby releasing the sutures from the lumen therein. The belt may be opened by splitting the casing along a perforated line, or other means may be employed to open the belt, such as having a sealable closure or other device disposed upon the belt. Once the belt is removed and the two vessels have been brought together, the buckle is utilized to organize the sutures and to enable a surgeon to then tie off the sutures in a conventional manner.

Figure 17:
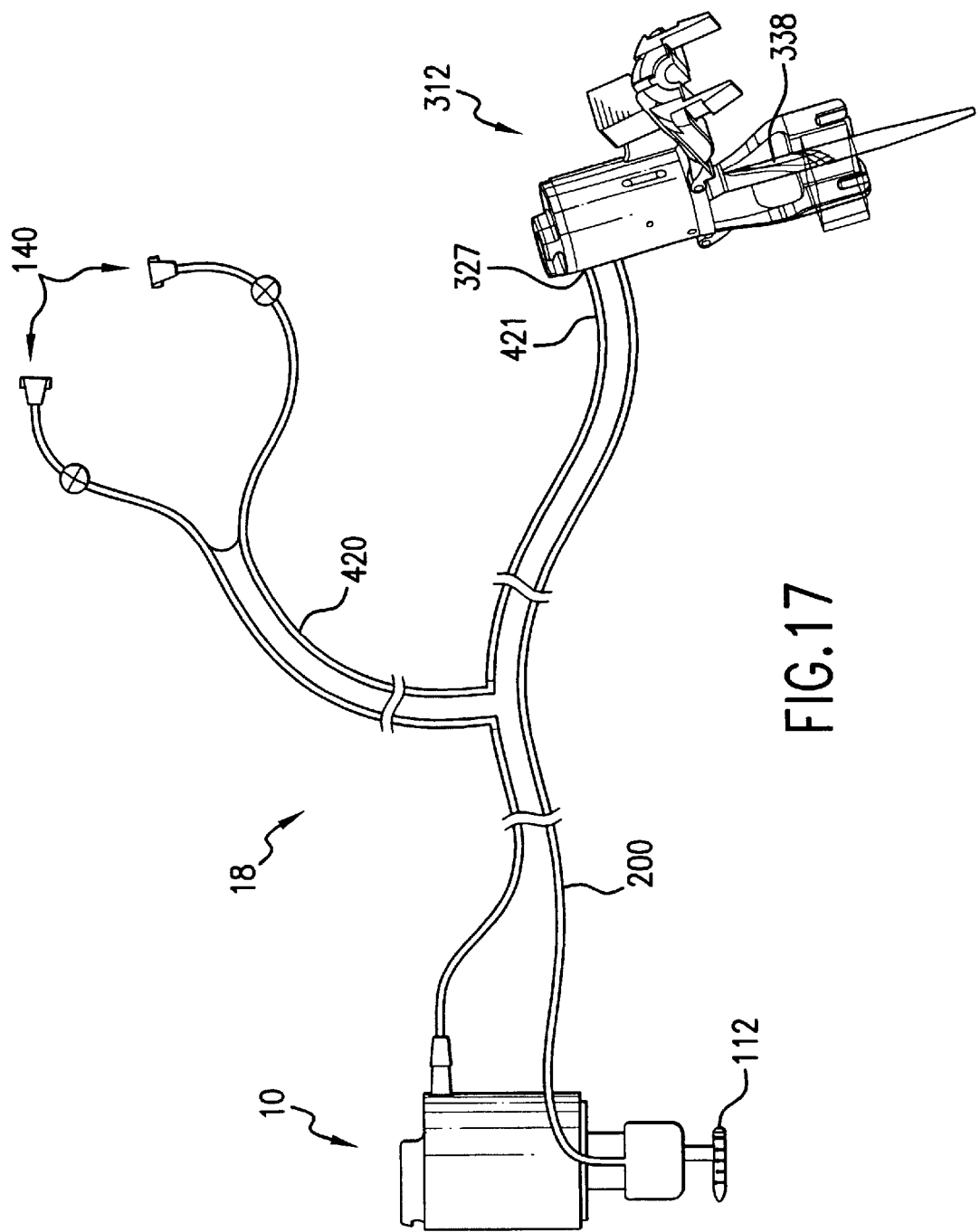
FIG. 17 is a side view of a system for performing end to side anastomoses utilizing the needle deployment device according to the present invention.

Referring now to FIG. 17 there is shown a second anastomosis system 18 in accordance with the present invention. As shown in FIG. 17 the anastomosis system 18 includes a needle deployment device, a belt, and a suture placement device.

Figure 18:
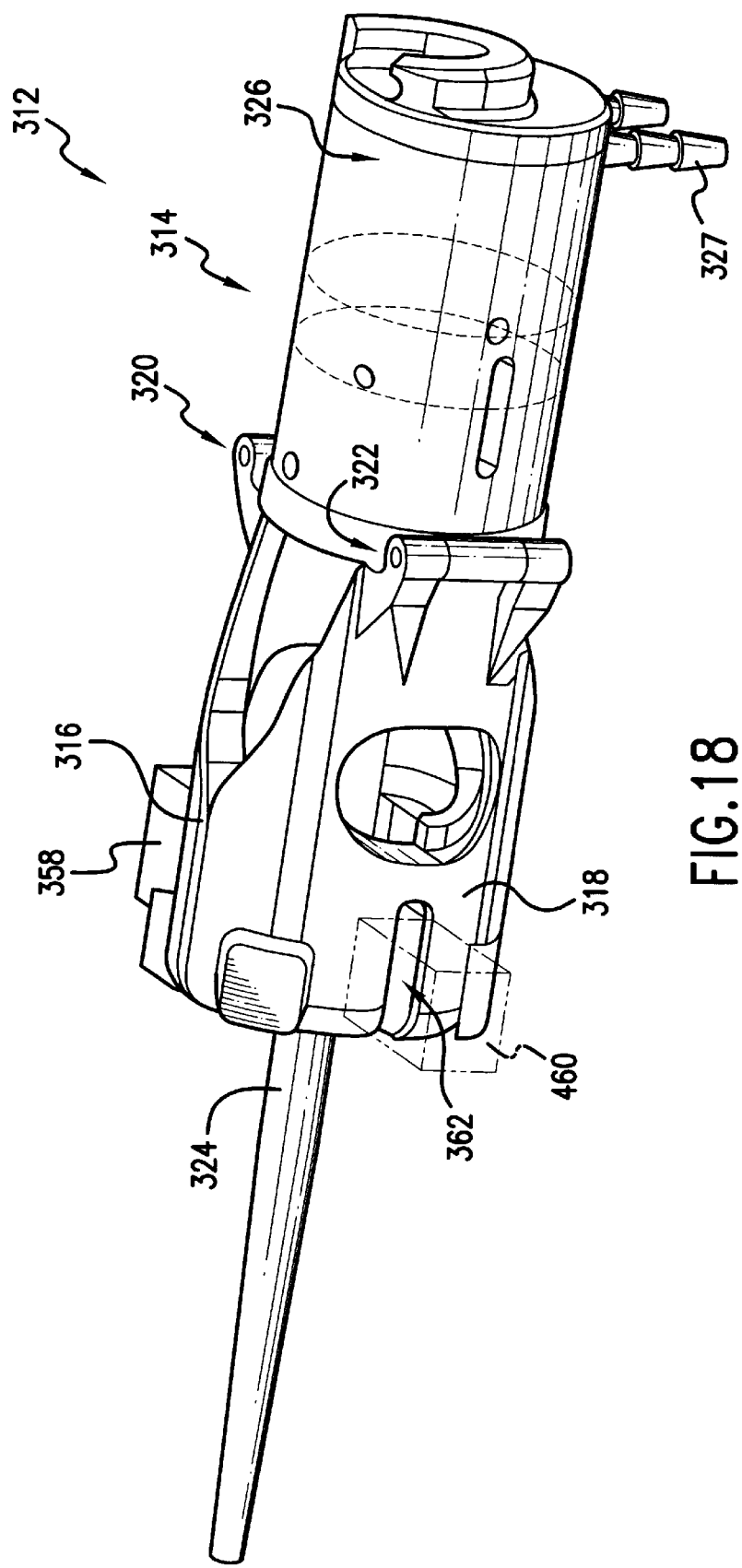
FIG. 18 is a isometric view of the device for deploying sutures through the end of a vessel or graft.

Referring to FIG. 18, the suture placement device 312 comprises a body 314 and two suture holder retainers 316, 318. Each retainer 316, 318 is mounted on the body 314 by means of a pivotal connection 320, 322 respectively. The device 312 further comprises a vessel support shaft 324 for receiving an end portion of a vessel, or graft, or the like, thereon. The shaft 324 is mounted on the body 314. The shaft 324 is arranged to be passed through the mouth of the vessel so that the vessel can be supported at an operative position on the shaft 324 at which position the device 312 can pass a plurality of suture elements through the wall of the vessel adjacent its mouth.

The body 314 comprises a piston and cylinder arrangement similar to that of the needle deployment device 10 described above. The piston and cylinder arrangement is indicated schematically and generally by reference numeral 326. A socket for receiving an end of the conduit portion 421 of the flexible elongate member 420 is indicated at 327. When the conduit portion 421 is connected to the socket 327, a chamber within the body 314 is connected in fluid flow communication with a female Luer-type connector.

Figure 19:
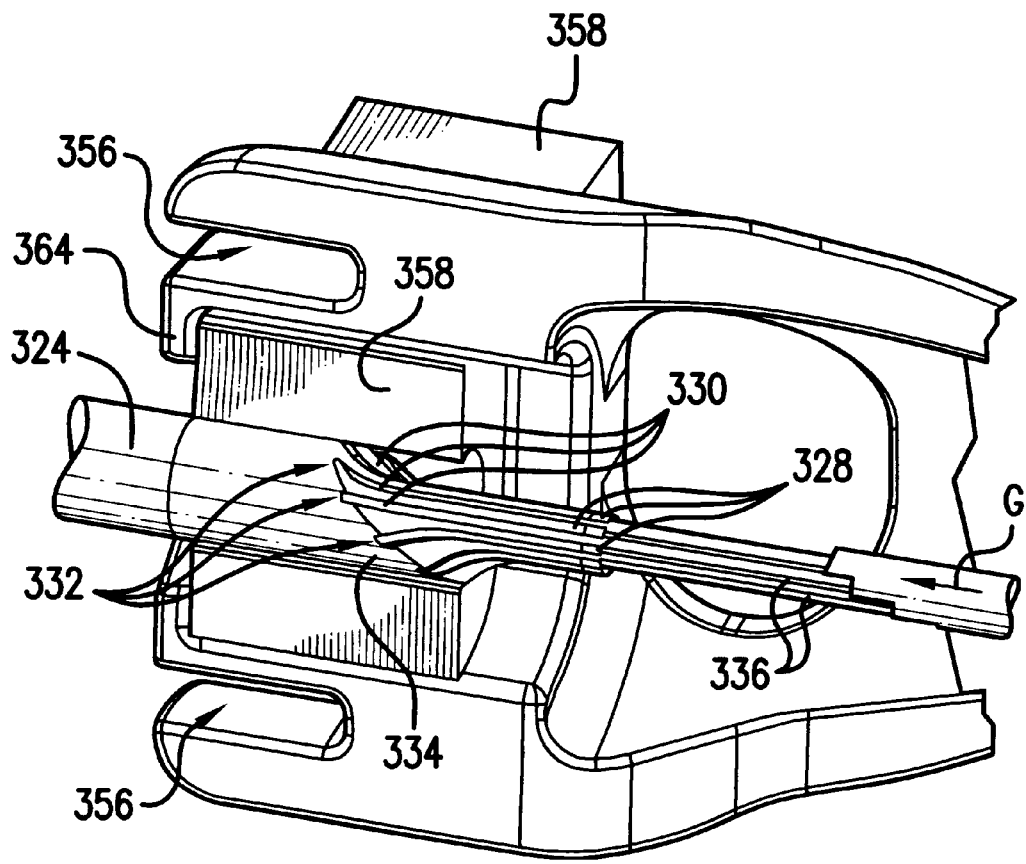
FIG. 19 shows, at an enlarged scale, part of the device shown in FIG. 18, a suture holder retainer of the suture placement device being shown in an open condition.
Figure 20:
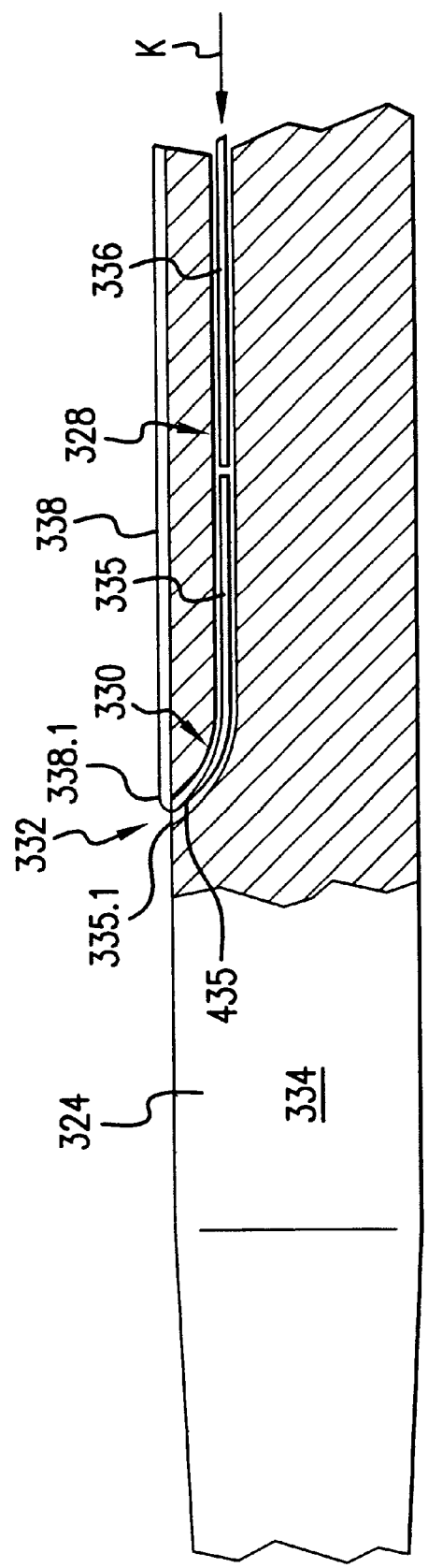
FIG. 20 shows, at an enlarged scale, a schematic part sectional side view of part of a vessel support shaft of the suture placement device, a needle of the suture placement device being shown in a dormant position within a passage defined in the shaft.
Figure 21:
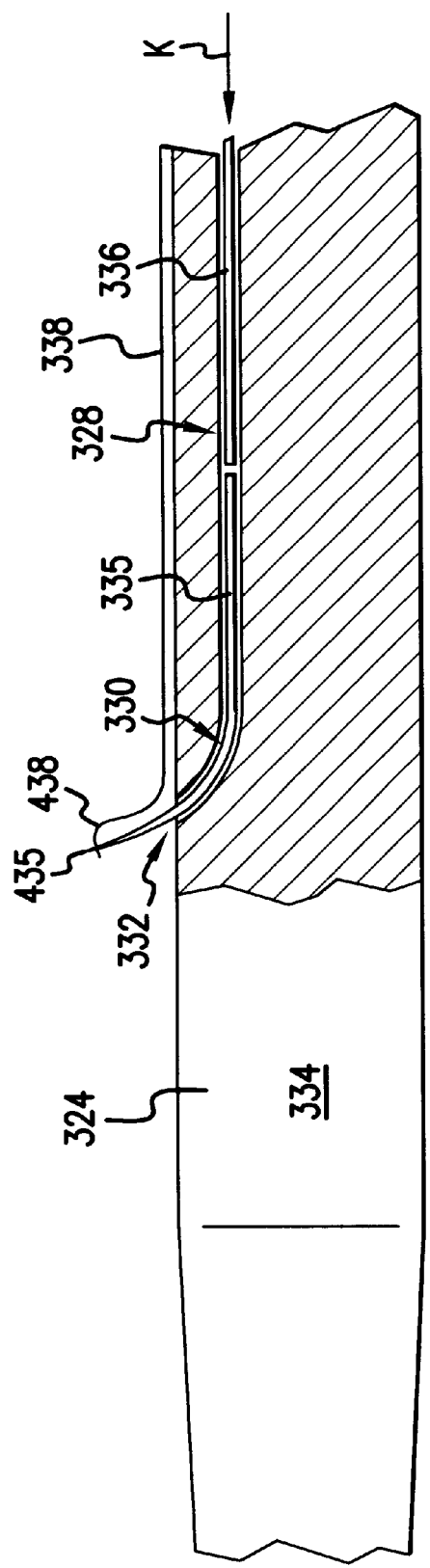
FIG. 21 shows a schematic part sectional side view corresponding to FIG. 20, the needle of the suture placement device having been displaced from its dormant position to an extended position.

Referring now to FIGS. 19 to 21 of the drawings, the shaft 324 defines a plurality of longitudinally extending passages indicated schematically by reference numeral 328. The passages 328 have bends 330 leading to mouths 332 opening at an outer surface 334 of the shaft 324. As can best be seen with reference to FIGS. 20 and 21, a needle 335 is received in each of the passages 328. Each needle 335 defines a pointed end 435. An actuation member in the form of an elongate pin or rod formation 336 is received in each of the passages 328 immediately behind the needles 335. The pin formations 336 are operatively associated with the piston on the body 314 so that the formations 336 are caused to advance, as indicated by arrow K, in response to the piston being caused to advance within its associated cylinder. It will be appreciated that the piston of the device 312 is caused to advance within its associated cylinder in a manner similar to that of the piston and cylinder arrangement of the needle deployment device 10, as described above, namely, by depressing a plunger of a syringe connected in fluid flow communication with the female Luer-type connector 140, as can best be seen with reference to FIG. 18.

With reference to FIG. 21, upon advancement of the pin formations 336 along the passages 328, the needles 335 are caused to advance along the passages 328 also. The needles 335 are caused to advance such that their pointed ends 435 are pushed out of the mouths 332 and laterally outwardly from the surface 334 of the shaft 324.

Figure 22:
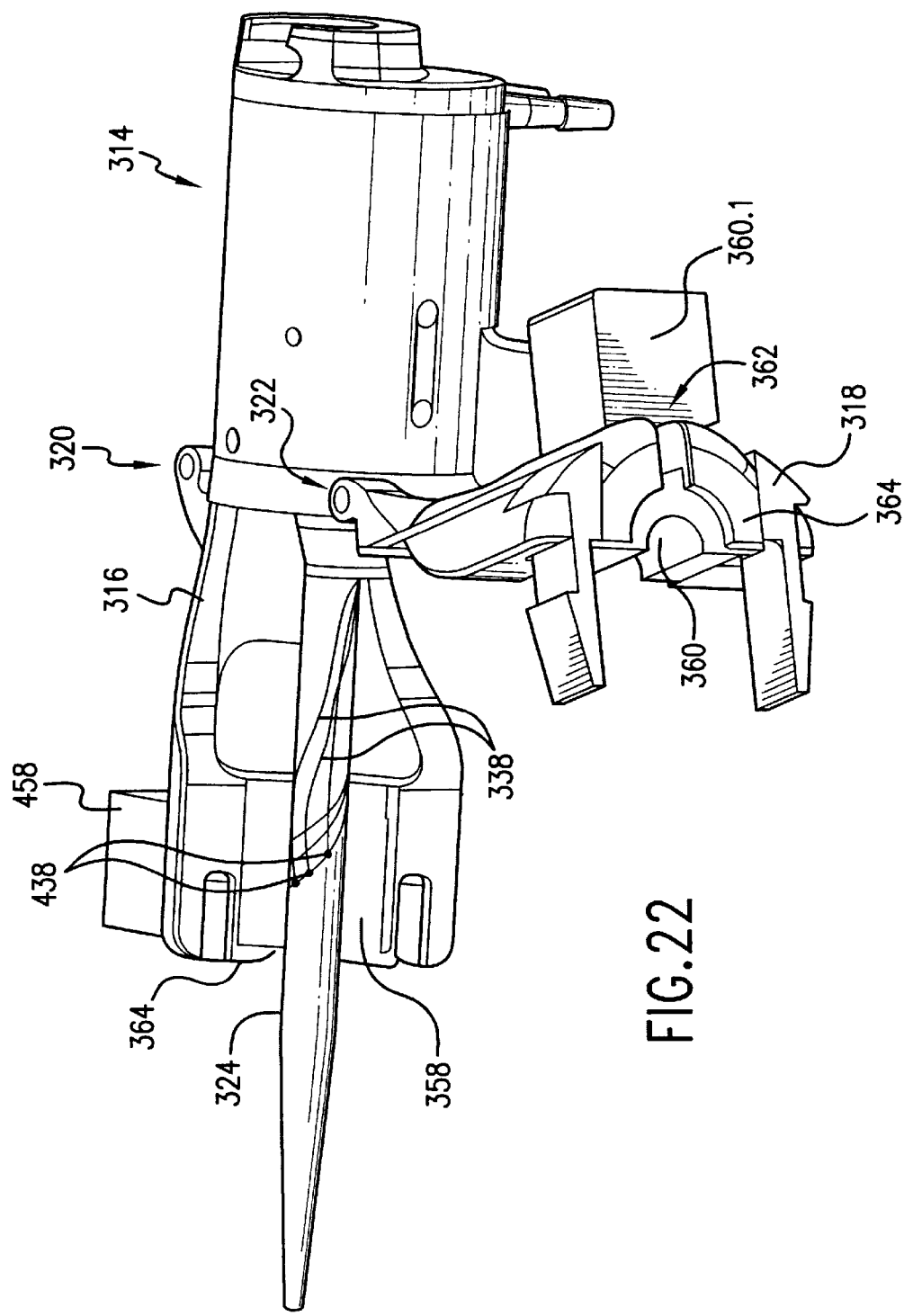
FIG. 22 shows a schematic three-dimensional view corresponding to FIG. 18, a suture holder retainer of the suture placement device being shown in an open condition and further showing a plurality of suture elements, end portions of which are attached to ends of needles.

Referring now to FIG. 22 of the drawings, ends 438 of a plurality of suture elements 338 are operatively engaged to end portions of the needles 335 adjacent the ends 435 of the needles 335. The ends 438 of the suture elements 338 can be operatively engaged to the end portions of the needles 335 in any appropriate manner. For example, the end portions of the needles 335 can have laterally extending apertures through which end portions of the suture elements 338 can be threaded. The suture elements 338 typically extend along the outer surface 334 of the shaft 324, along an outer surface of the body 314 and into the suture container portion 421 of the elongate flexible member 120, as can best be seen with reference to FIG. 17 of the drawings, in a fashion similar to that described above with reference to the system 15. It will be appreciated that opposed ends of the suture elements 338 are held on the suture support 118 of the device 112 of the system 310 in a fashion similar to that of the ends 460 of the suture elements 160 of the system 110.

The operation of the device 312 will now be described with reference to FIGS. 23 to 25 of the drawings. It will be appreciated that opposed ends of the suture elements 338 are placed through a vessel wall by means of the needle deployment device 10 and adjacent an incision in that vessel wall in a manner similar to that described above with reference to the system 15.

Figure 23:
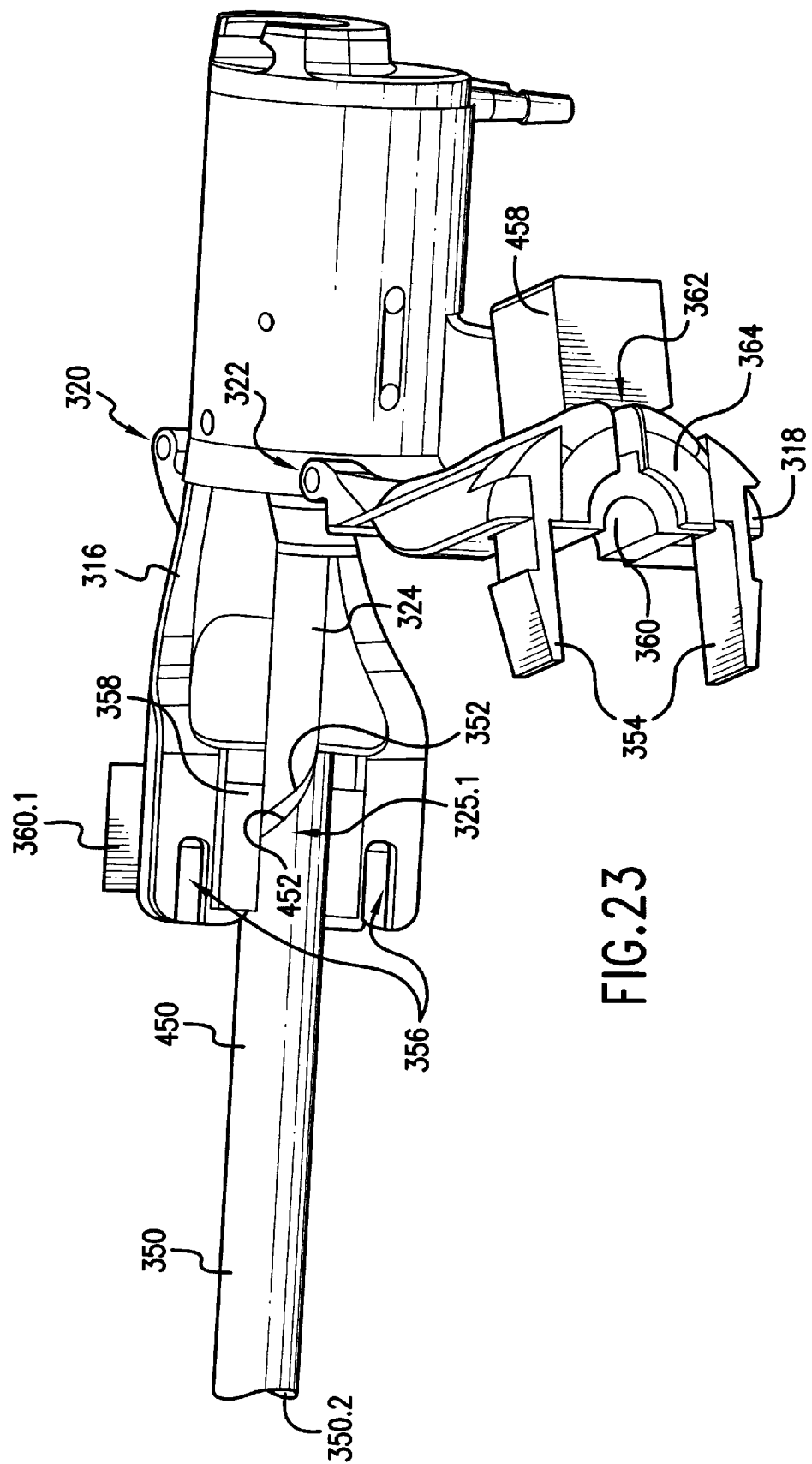
FIG. 23 shows a schematic three-dimensional view corresponding to FIG. 22, and shows an end portion of a vessel or graft received on the vessel support shaft of the suture placement device.

Referring to FIG. 23, an end portion 450 of a vessel, or graft, indicated generally by reference numeral 350, is shown in a received condition on the shaft 324. The end portion 450 of the vessel 350 was positioned on the shaft 324 by displacing the suture holder arrangements 316, 318 angularly about the pivotal connections 320, 322 into open positions and then passing the end portion 450 of the vessel 350 over the shaft 324. Conveniently, marks 352 are provided on the shaft 324 to indicate an appropriate position of an end 450 of the vessel 350 on the shaft 334 so as to enable the suture elements to be passed through a vessel wall 451 of the vessel 350 at an appropriate distance from the end 452. In FIG. 23, only the suture holder retainer 318 is shown in an open condition. Typically, both retainers 316, 318 are opened so as to pass the vessel portion 450 over the shaft 324. When the end portion 450 of the vessel 350 has been positioned such that its end 452 is in register with the marks 352 on the shaft 324, the retainers 316, 318 are displaced angularly about the pivotal connections 320, 322 into a closed condition in which the end portion 450 of the vessel 350 is embraced between the retainers 316, 318 and the shaft 324. FIG. 25 shows the retainer 316 having been displaced from an open condition into a closed condition after the portion 450 of the vessel 350 has been appropriately positioned on the shaft 324.

Figure 28:
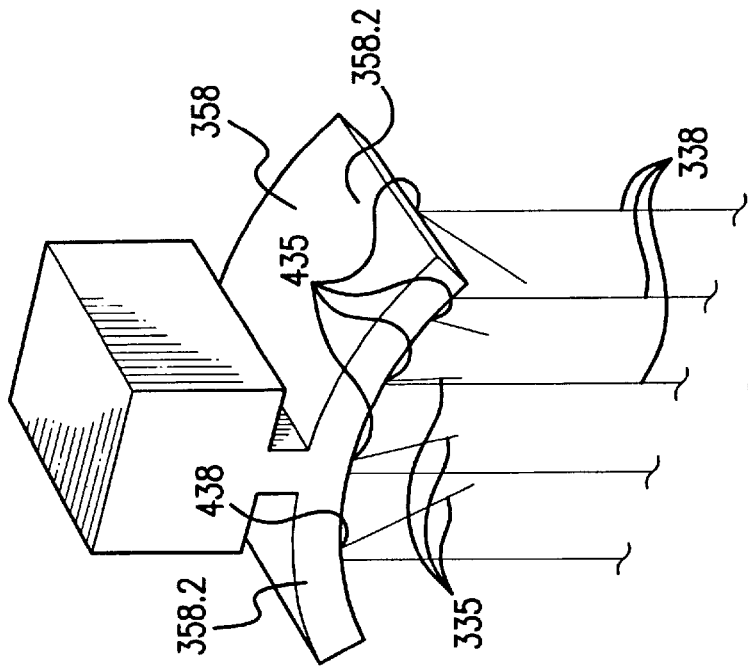
FIG. 28 shows a schematic three-dimensional view of the suture holder of FIG. 27 having a shape corresponding to its shape when in a relaxed condition after having been removed from its associated suture holder retainer.

Conveniently, the vessel 350 is shaped to have an angled, or inclined, end 452 so as to permit an end-to-side anastomosis to be formed in which the one vessel extends from the other at an acute angle, as can best be seen with reference to FIG. 28 of the drawings. The marks 352 are formed on the shaft 324 to extend circumferentially around the shaft 324 so as to align with a vessel having such an inclined end 452.

Figure 24:
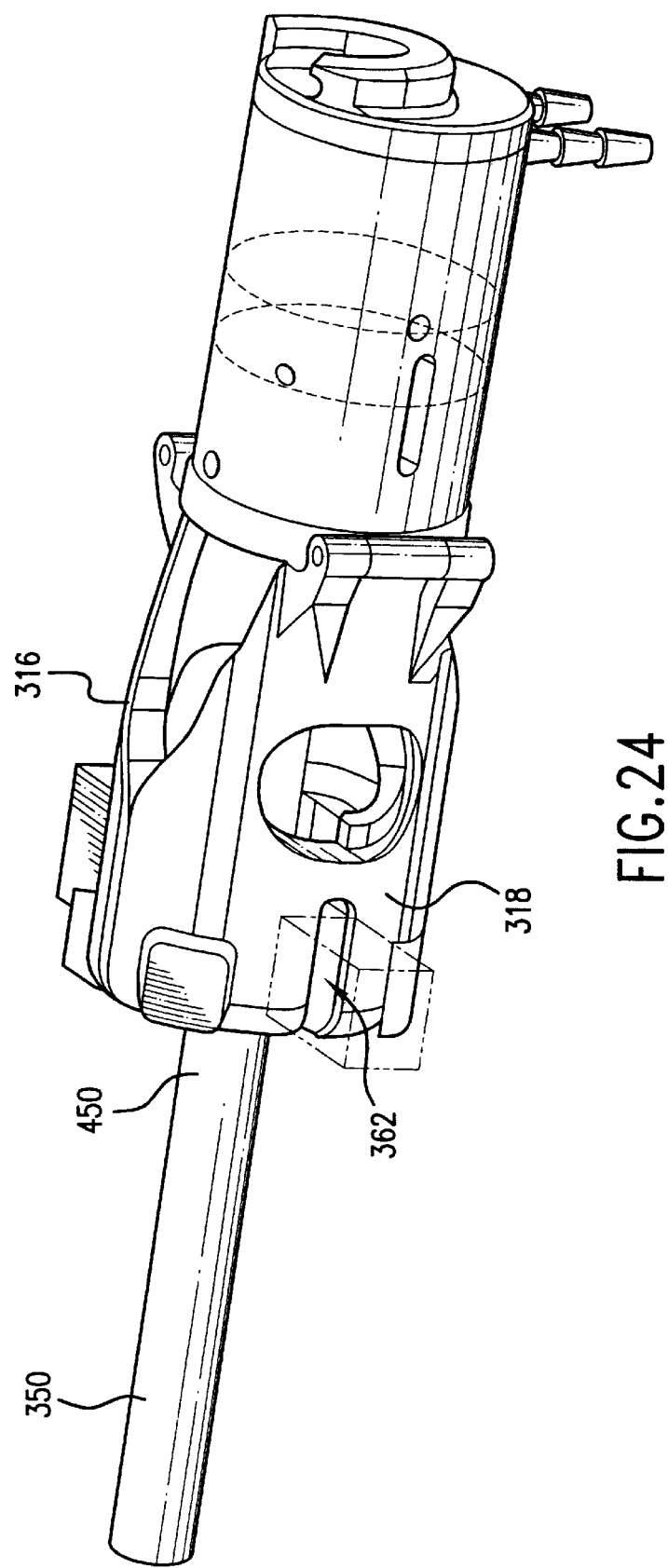
FIG. 24 shows a schematic three-dimensional view corresponding to FIG. 23 and shows the suture holder retainer in a closed condition after the end portion of the vessel or graft has been positioned on the vessel support shaft.
Figure 25:
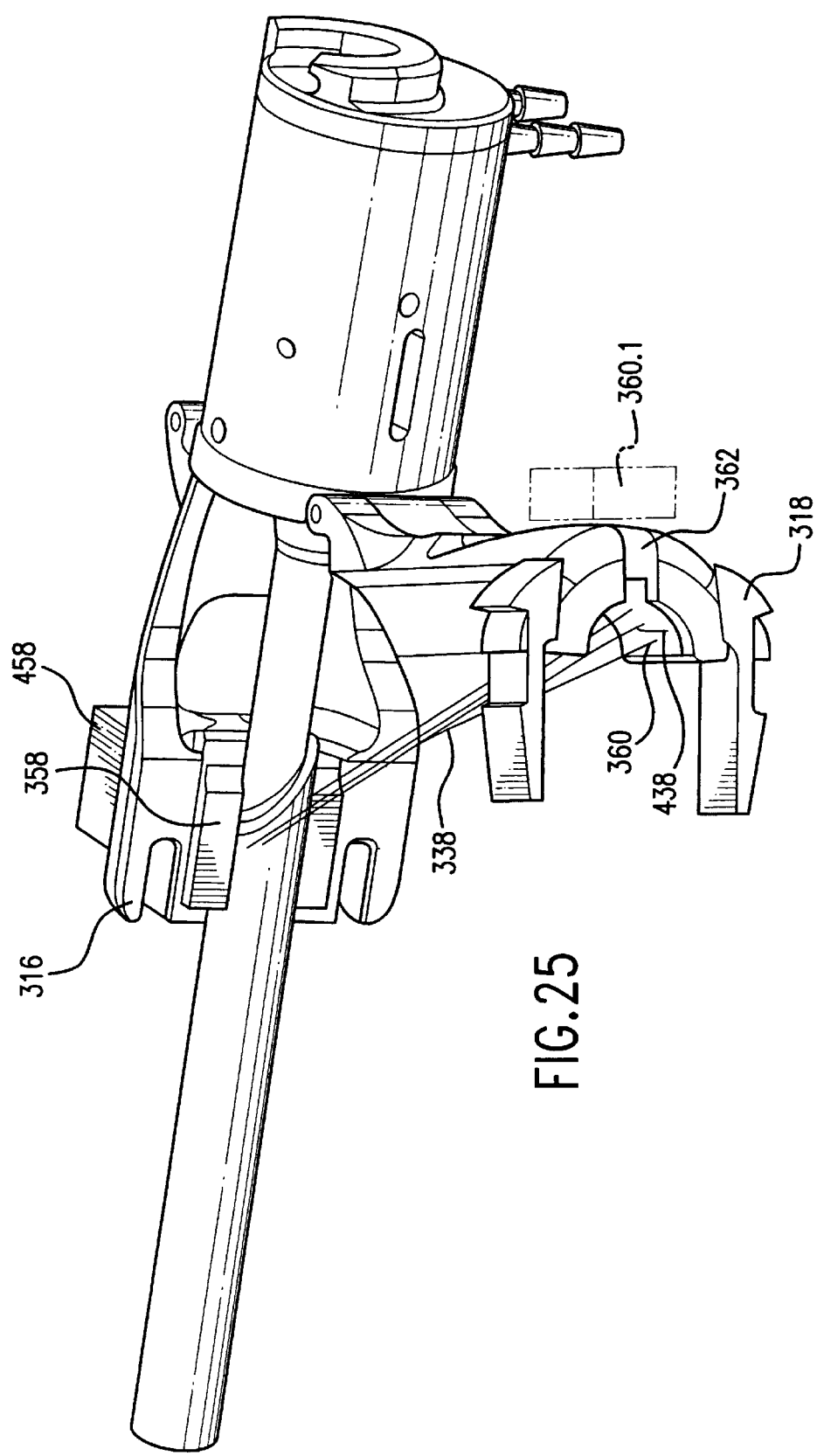
FIG. 25 shows a schematic three-dimensional view corresponding to FIG. 24, the suture holder retainer being shown in an open condition and further showing the needles having been passed through the vessel or graft adjacent a mouth of the vessel or graft supported on the vessel support shaft.
Figure 26:
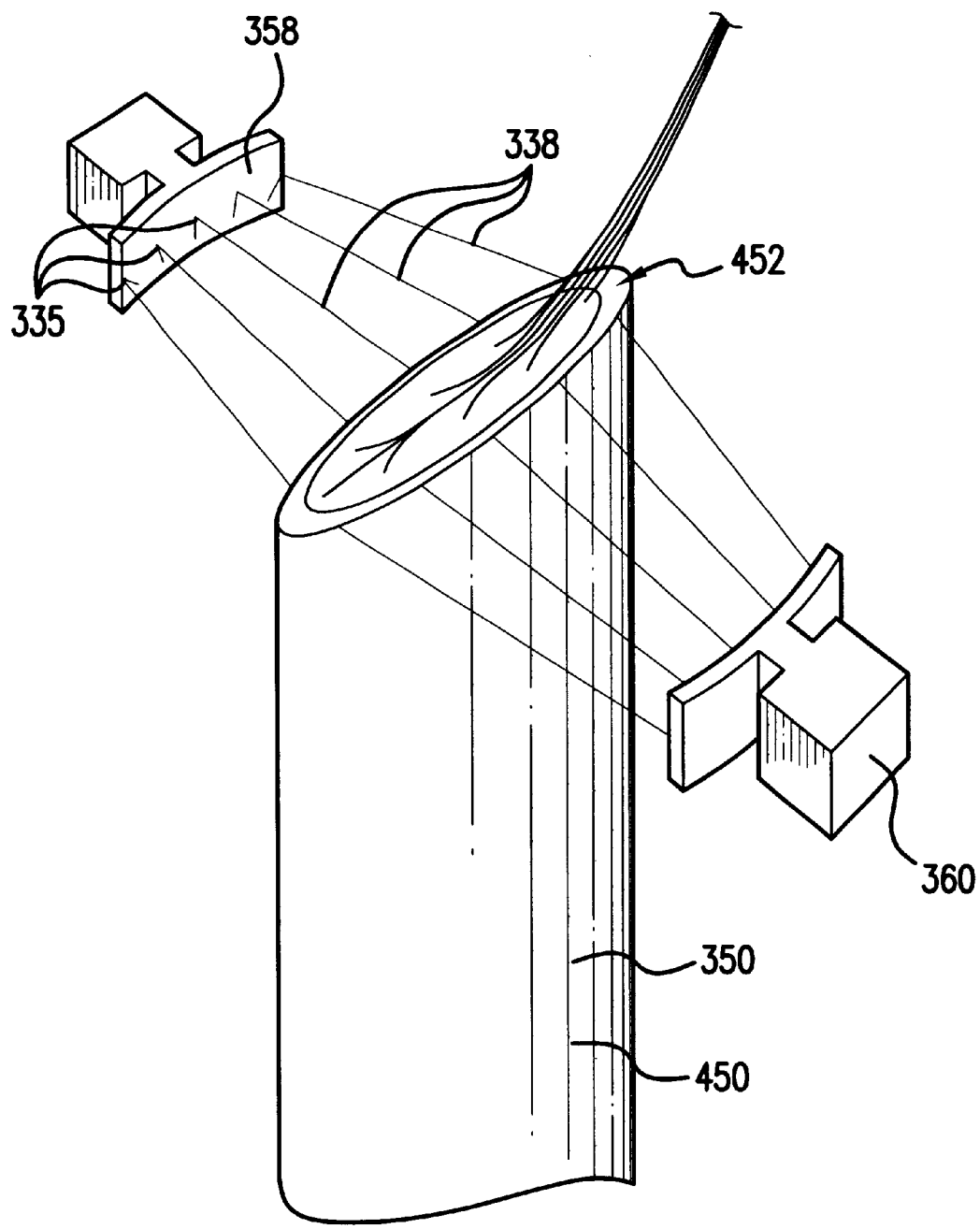
FIG. 26 shows a schematic three-dimensional view of the end portion of the graft, after the needles of the suture placement device have been passed through the graft adjacent its mouth, the needles being held on suture holders of the suture placement device, the suture holders having been removed from the suture holder retainers of the suture placement device.

FIG. 24 shows the portion 450 of the vessel 350 having been received on the shaft 324 and further shows both retainers 316, 318 in closed conditions. As can best be seen with reference to FIG. 23 of the drawings, the retainers 316, 318 are provided with cooperating engaging formations so as to lockingly engage with each other when in their closed conditions. Conveniently, the engaging formations comprise tongue members 354, 354 and slot arrangements 356, 356 for snap-lockingly receiving the tongue members 354, 354. After the end portion 450 of the vessel 350 has been received on the shaft 324 and the retainers 316, 318 have been closed so as to engage lockingly with each other, the needles 335 bearing the ends 438 of the suture elements 338 are caused to advance along the passages 328. This is achieved by means of the pin formations 336 being displaced along the passages 328 in response to actuating a syringe connected in fluid flow communication with the female Luer-type connector 140 operatively associated with the device 312. As the needles 335 are caused to advance in this fashion, the ends 435 of the needles 335 are driven through the wall 451 of the vessel 350 adjacent its mouth. The ends 438 of the suture elements 338 are passed through the vessel wall 451 together with the ends 435 of the needles 335, since the ends 438 of the suture elements 338 are appropriately attached to the ends of the needles. After the ends 435 of the needles 335 have passed through the vessel wall 452, the ends 435 are driven into suture holders 358, 360 releasably mounted on the suture holder arrangements 316, 318 to be held captive by the holders 358, 360. The retainers 316, 318 are then angularly displaced about the pivotal connections 320, 322 into their open conditions to enable the vessel 350 to be removed from the shaft 324. The suture holders 358, 360 are removed from the retainers 316, 318, while the needle ends 435, and consequently also the ends 438 of the suture elements 338, are held captive on the suture holders 358, 360. To remove the holders 358, 360 from the retainers 316, 318, hand grippable portions 450, 360.1 of the holders 358, 360 are typically manipulated to cause the holders 358, 360 to be slid along slots 362 defined by the retainers 316, 318. As can best be seen in FIG. 22 of the drawings, each retainer 316, 318 has a part annular shoulder formation 364 arranged to retain the holders 358, 360 in a mounted condition on the retainers 316, 318. When the holders 358, 360 are removed from their associated retainers 316, 318, the hand grippable portions 458, 460 are manipulated resiliently to urge the holders over the annular shoulder formations 364. FIG. 26 shows the end portion 450 of the vessel 350 having been removed from the shaft 324 and further shows the holders 358, 360 having been removed from the associated retainers 316, 318.

Figure 27:
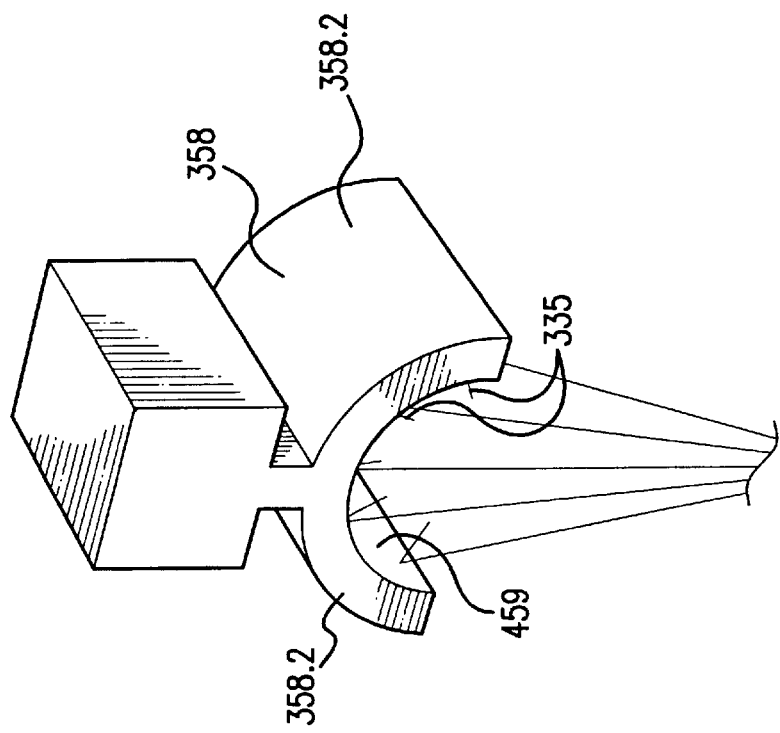
FIG. 27 shows a schematic three-dimensional view of one of the suture holders normally retained on an associated suture holder retainer of the device, the suture holder being shown having a shape corresponding to its shape when retained on its associated suture holder retainer.
Figure 29:
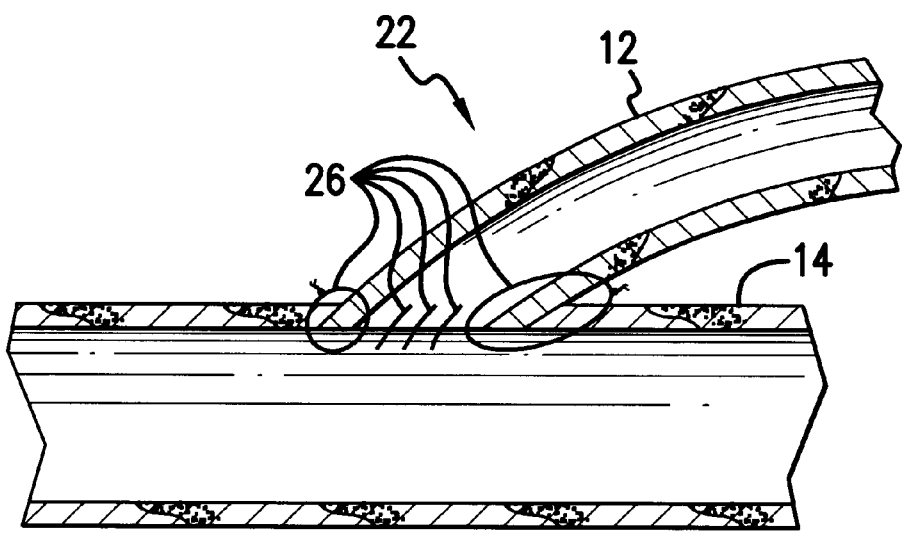
FIG. 29 is a cross-sectional side view illustrating a end to side anastomosis.

Referring now to FIGS. 27 and 28 of the drawings, the suture holder 358 is shown in greater detail, and after it has been removed from its associated retainer 316. In FIGS. 27 and 28, the holder 358 is shown after the needles 335 have been passed through the portion of the vessel 350 and into engagement with the holder 358. In FIG. 27, the suture holder is shown having a shape corresponding to the shape which it has when mounted on its associated retainer 316. When mounted on the retainer 316, opposed flange portions 358.2 of the suture holder 358 are held in a resiliently deformed condition such that an inner surface 459 defined by the flange portions 458 extends generally along a circular circumference so as to extend snugly around the vessel portion 450 when held between the retainers 316, 318 and the shaft 324. The suture holder 358 is typically made from a resilient material, such as silicone, or the like. In FIG. 27, the suture holder 358 is shown after having been removed from its associated retainer 316. After having been removed, the flange portions 459 take up a relaxed condition in which they have a straighter profile than in the case when mounted on the retainer 316. In this relaxed condition, the spacing between the needle ends 335 on which the ends 435 of the suture elements 338 are carried is greater than in the case when the holder 358 was mounted on the retainer 316. The holder 358 is designed so that when in its relaxed condition, the spacing between adjacent suture element ends 435 on the needles 335 generally corresponds with the spacing between adjacent suture element ends when held on the needle block assembly 70 and 70" of the suture guide 40 and 40' of the needle deployment device 10.

To form the end-to-side anastomosis, the needle deployment device 10 is used to place the opposed ends of the suture elements 338 through another vessel wall adjacent an incision in the other vessel wall in a fashion similar to that described above with reference to the system 15.

After the suture elements 338 have been placed through the wall of the portion 450 of the vessel 350 adjacent its mouth, as described above, and after opposed ends of the suture elements 338 have been placed through a vessel wall adjacent an incision in the vessel wall by the needle deployment device 10, in a manner similar to that described above, the suture holders 358, 360 are paired up with the suture attached to the proximal end portion of the needles 78 of the needle deployment device 10. Conveniently, the holders may be distinctively colored to indicate to the user which of the holders is to be matched up with which of the holders. Accordingly, in this fashion, opposed ends of the same suture elements are paired up with each other. The paired up end portions of the suture elements can then be passed into the slots of a suture handling device as described above, for example. After having been received in the slots of the suture handling device as described above, the suture elements can be removed from the suture handling device and can be tied, or otherwise secured together, so as to form sutures between the vessels thereby to form an end-to-side anastomosis between the vessels.

Although the present invention has been described in considerable detail with reference to certain preferred embodiments, it is contemplated that one skilled in the art may make modifications to the device herein without departing from the scope of the invention. Therefore, the scope of the amended claims should not be considered limited to the embodiments described herein.

What is claimed is:

1. A suturing device comprising:
 a suture guide including a shaft portion having a vertical axis, and a foot portion having an axis at an angle relative to the vertical axis of the shaft portion, the foot portion including a plurality of suture holders defined along its length, each suture holder holding a suture; and a guide assembly housing movably holding at least one needle relative to a first side of the foot portion and movably holding at least one needle relative to a second side of the foot portion, wherein each needle has a distal end portion movable into a respective suture holder at an angle relative to the vertical axis of the shaft portion such that the distal end portion moves toward the shaft portion when moving into the respective suture holder.

2. The device of claim 1, further comprising a body including a driving mechanism and wherein the needles are operatively associated with the driving mechanism.

3. The device of claim 2, wherein the driving mechanism drives the needles into the foot portion.

4. The device of claim 1, wherein the foot portion has a circular cross-sectional profile.

5. The device of claim 1, wherein the foot portion has an oval cross-sectional profile.

6. The device of claim 1 wherein the shaft portion is slidably engaged with the guide assembly housing and wherein the foot portion extends from the shaft portion.

7. The device of claim 1, wherein the sutures further include cuffs, and the cuffs are adapted to receive the needles.

8. A method of suturing an incision in a vessel wall, the method comprising:

providing a suture guide having shaft portion having a vertical axis, and a foot portion having an axis at an angle relative to the vertical axis of the shaft portion, the foot portion having a generally circular cross-section and a plurality of suture holders defined along a length of the foot portion;

placing the foot portion of the suture guide through the incision;

advancing a plurality of needles having tips through the vessel wall and into suture holders of the foot portion at an angle relative to the vertical axis of the shaft portion such that the tips move toward the shaft portion when moving into the respective suture holder;

receiving the needle tips into cuffs releasably held in the suture holders, the cuffs having suture elements attached thereto; and retracting the plurality of needles from the foot portion so as to pull the cuffs and suture elements through the vessel wall.

9. The method of claim 8 further comprising aligning a graft vessel with the incision, and advancing suture through an end region of the graft vessel such that the graft vessel is joined with the vessel wall to provide an anastomosis.

* * * * *